(12) United States Patent
Wabl

(10) Patent No.: US 10,793,829 B2
(45) Date of Patent: Oct. 6, 2020

(54) TRANSGENIC MAMMALS AND METHODS OF USE THEREOF

(71) Applicant: Trianni, Inc, San Francisco, CA (US)

(72) Inventor: Matthias Wabl, San Francisco, CA (US)

(73) Assignee: TRIANNI, INC., San Francisco, CA (US)

( * ) Notice: Subject to any disclaimer, the term of this patent is extended or adjusted under 35 U.S.C. 154(b) by 234 days.

(21) Appl. No.: 15/603,347

(22) Filed: May 23, 2017

(65) Prior Publication Data

US 2017/0303517 A1     Oct. 26, 2017

Related U.S. Application Data

(63) Continuation-in-part of application No. 13/818,184, filed as application No. PCT/US2011/045333 on Jul. 26, 2011.

(60) Provisional application No. 61/367,809, filed on Jul. 26, 2010, provisional application No. 62/340,243, filed on May 23, 2016.

(51) Int. Cl.
| | |
|---|---|
| *A01K 67/027* | (2006.01) |
| *C12N 5/0735* | (2010.01) |
| *C07K 16/46* | (2006.01) |
| *C12N 15/85* | (2006.01) |

(52) U.S. Cl.
CPC .......... *C12N 5/0606* (2013.01); *C07K 16/462* (2013.01); *C12Y 304/24046* (2013.01); *A01K 67/0275* (2013.01); *A01K 2217/072* (2013.01); *A01K 2227/105* (2013.01); *A01K 2267/01* (2013.01); *C07K 2317/24* (2013.01); *C07K 2317/52* (2013.01); *C07K 2317/56* (2013.01); *C12N 2015/8518* (2013.01); *C12N 2510/00* (2013.01)

(58) Field of Classification Search
CPC .................................................. A01K 67/0275
See application file for complete search history.

(56) References Cited

U.S. PATENT DOCUMENTS

| | | | |
|---|---|---|---|
| 4,892,824 A | 1/1990 | Skaletsky | |
| 5,591,669 A | 1/1997 | Krimpenfort et al. | |
| 5,593,598 A | 1/1997 | McGinness et al. | |
| 5,612,205 A | 3/1997 | Kay et al. | |
| 5,633,425 A | 5/1997 | Lonberg et al. | |
| 5,661,016 A | 8/1997 | Lonberg et al. | |
| 5,789,215 A | 8/1998 | Berns et al. | |
| 5,789,650 A | 8/1998 | Lonberg et al. | |
| 5,814,318 A | 9/1998 | Lonberg et al. | |
| 5,874,299 A | 2/1999 | Lonberg et al. | |
| 5,877,397 A | 3/1999 | Lonberg et al. | |
| 5,939,598 A | 8/1999 | Kucherlapati et al. | |
| 5,985,615 A | 11/1999 | Jakobovits et al. | |
| 6,023,010 A | 2/2000 | Krimpenfort et al. | |
| 6,091,001 A | 7/2000 | Jakobovits et al. | |
| 6,114,598 A | 9/2000 | Kucherlapati et al. | |
| 6,130,364 A | 10/2000 | Jakobovits et al. | |
| 6,162,963 A | 12/2000 | Kucherlapati et al. | |
| 6,492,575 B1 | 12/2002 | Wagner et al. | |
| 6,570,061 B1 | 5/2003 | Rajewsky et al. | |
| 6,586,251 B2 | 7/2003 | Economides | |
| 6,596,541 B2 | 7/2003 | Murphy | |
| 6,653,113 B1 | 11/2003 | Berns et al. | |
| 6,673,986 B1 | 1/2004 | Kucherlapati et al. | |
| 6,998,514 B2 | 2/2006 | Bruggeman | |
| 7,041,870 B2 | 5/2006 | Kazuma et al. | |
| 7,041,871 B1 | 5/2006 | Lonberg | |
| 7,064,244 B2 | 6/2006 | Jakobovits et al. | |
| 7,105,348 B2 | 9/2006 | Murphy | |
| 7,129,084 B2 | 10/2006 | Buelow | |
| 7,145,056 B2 | 12/2006 | Jakobovits | |
| 7,205,148 B2 | 4/2007 | Economides et al. | |
| 7,294,754 B2 | 11/2007 | Poueymirou et al. | |
| 7,473,557 B2 | 1/2009 | Economides et al. | |
| 7,476,536 B2 | 1/2009 | Kuroiwa et al. | |
| 7,501,552 B2 | 3/2009 | Lonberg | |
| 7,541,513 B2 | 6/2009 | Bruggeman | |
| 7,659,442 B2 | 2/2010 | Poueymirou et al. | |
| 7,868,223 B2 | 1/2011 | Tomizuka et al. | |
| 8,158,419 B2 | 4/2012 | Lonberg | |
| 8,232,449 B2 | 7/2012 | Tanamachi | |
| 8,293,480 B2 | 10/2012 | Lonberg | |
| 8,367,888 B2 | 2/2013 | Bruggeman | |
| 8,502,018 B2 | 8/2013 | Murphy | |
| 8,754,287 B2 | 6/2014 | MacDonald et al. | |

(Continued)

FOREIGN PATENT DOCUMENTS

| | | |
|---|---|---|
| CA | 2089661 C | 3/1992 |
| EP | 1399575 | 7/2006 |
| EP | 1399559 | 4/2008 |
| EP | 0817835 | 10/2008 |
| EP | 2264163 | 12/2010 |
| EP | 2517556 | 10/2012 |
| EP | 2517557 | 10/2012 |
| GB | 2398784 A | 9/2004 |
| GB | 2561352 A | 10/2018 |
| WO | 90/04036 A1 | 4/1990 |
| WO | 90/10077 A1 | 9/1990 |
| WO | 94/25585 A1 | 11/1994 |
| WO | 96/40915 A2 | 12/1996 |

(Continued)

OTHER PUBLICATIONS

Garcia-Arocena D. (2014, The Jackson Laboratory, Same Mutation, Different Phenotype?) (Year: 2014).*

(Continued)

*Primary Examiner* — Thaian N. Ton
*Assistant Examiner* — David A. Montanari
(74) *Attorney, Agent, or Firm* — Medler Ferro Woodhouse & Mills, PLLC

(57) ABSTRACT

The present invention relates to transgenic mammals that express bovine-based immunoglobulins, including transgenic rodents that express bovine-based immunoglobulins for the development of bovine therapeutic antibodies.

13 Claims, 11 Drawing Sheets

Specification includes a Sequence Listing.

(56) References Cited

U.S. PATENT DOCUMENTS

| | | | |
|---|---|---|---|
| 9,012,717 | B2 | 4/2015 | MacDonald et al. |
| 9,580,491 | B2 | 2/2017 | Green et al. |
| 10,575,504 | B2 | 3/2020 | Green et al. |
| 2003/0017534 | A1 | 1/2003 | Buelow |
| 2006/0015957 | A1 | 1/2006 | Lonberg |
| 2007/0061900 | A1 | 3/2007 | Murphy |
| 2009/0055943 | A1 | 2/2009 | Economides |
| 2009/0111126 | A1 | 4/2009 | Akamatsu |
| 2009/0136950 | A1 | 5/2009 | Dubridge |
| 2010/0317539 | A1 | 12/2010 | Yu |
| 2011/0145937 | A1 | 6/2011 | MacDonald et al. |
| 2011/0236378 | A1 | 9/2011 | Green |
| 2011/0258710 | A1 | 10/2011 | Murphy |
| 2011/0283376 | A1 | 11/2011 | Murphy |
| 2012/0047585 | A1 | 2/2012 | Rohrer et al. |
| 2012/0073004 | A1 | 3/2012 | MacDonald |
| 2012/0090041 | A1 | 4/2012 | Buelow |
| 2012/0096572 | A1 | 4/2012 | MacDonald et al. |
| 2013/0137101 | A1 | 5/2013 | Economides |
| 2013/0263292 | A1 | 10/2013 | Liang |
| 2013/0333057 | A1 | 12/2013 | MacDonald et al. |
| 2014/0283153 | A1 | 9/2014 | Trianni |
| 2015/0183820 | A1 | 7/2015 | Honda et al. |
| 2017/0058052 | A1 | 3/2017 | Wabl et al. |
| 2017/0218090 | A1 | 8/2017 | Green et al. |
| 2017/0226162 | A1 | 8/2017 | Killeen et al. |
| 2017/0306352 | A1 | 10/2017 | Wabl |
| 2018/0230238 | A1 | 8/2018 | Wabl et al. |

FOREIGN PATENT DOCUMENTS

| | | |
|---|---|---|
| WO | 99/45962 A1 | 6/1999 |
| WO | 01/09187 A2 | 2/2001 |
| WO | WO 02/12437 | 2/2002 |
| WO | 02/066618 A1 | 8/2002 |
| WO | WO 02/066630 | 8/2002 |
| WO | 2008/070367 A2 | 6/2008 |
| WO | 2008/081197 A1 | 7/2008 |
| WO | 2009/013620 A2 | 1/2009 |
| WO | 2009/157771 A2 | 12/2009 |
| WO | 2010/039900 A2 | 4/2010 |
| WO | WO 11/004192 | 1/2011 |
| WO | 2011/123708 A2 | 10/2011 |
| WO | WO 11/158009 | 12/2011 |
| WO | WO 11/163311 | 12/2011 |
| WO | WO 12/018610 | 2/2012 |
| WO | 2012/123949 A1 | 9/2012 |
| WO | 2013/022782 A1 | 2/2013 |
| WO | 2013/092720 A1 | 6/2013 |
| WO | 2013/138681 A1 | 9/2013 |
| WO | 2013/171505 A2 | 11/2013 |
| WO | 2014/013075 A2 | 1/2014 |
| WO | 2015/112790 A2 | 7/2015 |
| WO | 2015/188141 A2 | 12/2015 |
| WO | 2017/095939 A1 | 6/2017 |
| WO | 2018/189520 A1 | 10/2018 |

OTHER PUBLICATIONS

Heimain-Patterson et al. (2011, Amyotrophic Lateral Schlerosis, vol. 00, pp. 1-8) (Year: 2011).*
2004, Barthold S., Genetica, vol. 122, pp. 75-88 (Year: 2004).*
Tong et al. (2010, Nature, vol. 467(7312), pp. 211-213) (Year: 2010).*
Hong et al. (2012, Stem Cells and Development, vol. 21(9), pp. 1571-1586) (Year: 2012).*
Altschul et al., "Basic local alignment search tool," *J Mol Biol* 215:403-410 (1990).
Bentley et al., "Unrearranged immunoglobulin variable region genes have a functional promoter," *Nucleic Acids Res* 10:1841-1856 (1982).
Casellas et al., "Igκ allelic inclusion is a consequence of receptor editing," *J Exp Med* 204(1):153-160 (2007).
Cesari et al, "Elk-1 knock-out mice engineered by Flp recombinase-mediated cassette exchange," *Genesis* 38:87-92 (2004).
Church et al., "Lineage-specific biology revealed by a finished genome assembly of the mouse," *PLoS Biol* 7:e1000112 (2009).
Clarke et al., "An immunoglobulin promoter region is unaltered by DNA rearrangement and somatic mutation during B-cell development," *Nucleic Acids Res* 10:7731-7749 (1982).
Decaire et al., "A Publicly Available PCR Methods Laboratory Manual and Supporting Material," *J Microbiol Biol Educ* 16:269-270 (2015).
Downing et al., "Technical assessment of the first 20 years of research using mouse embryonic stem cell lines," *Stem Cells* 22:1168-1180 (2004).
Doyen et al., "Analysis of promoter and enhancer cell type specificities and the regulation of immunoglobulin gene expression," *Gene* 50:321-331 (1986).
Fishwild et al., "High-avidity human IgG kappa monoclonal antibodies from a novel strain of minilocus transgenic mice," *Nat Biotechnol*, 14:845-851 (1996).
Gellert, "Molecular analysis of V(D)J recombination," *Annu Rev Genet* 26:425-446 (1992).
Gopal et al., "Contribution of promoter to tissue-specific expression of the mouse immunoglobulin kappa gene," *Science* 229:1102-1104 (1985).
Hengartner et al., "Assignment of genes for immunoglobulin kappa and heavy chains to chromosomes 6 and 12 in mouse," *Proc Natl Acad Sci USA* 75:4494-4498 (1978).
Honjo et al., ed. *Immunoglobulin Genes*. San Diego, CA: Academic Press Inc., 1989; Chapters 4-6 and 17.
Hosseini et al., "Duplicated copies of the bovine JH locus contribute to the Ig repertoire," *Int Immunol* 16(6):843-852 (2004).
International Human Genome Sequencing Consortium, "Finishing the euchromatic sequence of the human genome," *Nature* 431:931-945 (2004).
Jones et al., "Replacing the complementarity-determining regions in a human antibody with those from a amouse," *Nature* 321:522-525 (1986).
Jung et al., "Unraveling V(D)J Recombination: Insights into Gene Regulation," *Cell* 116:299-311 (2004).
Kabat et al., "Variable region genes for the immunoglobulin framework are assembled from small segments of DNA—A hypothesis," *Proc Natl Acad Sci USA* 75:2429-2433 (1978).
Kabat et al., "Evidence supporting somatic assembly of the DNA segments (minigenes), coding for the framework, and complementarity-determining segments of immunoglobulin variable regions," *J Exp Med* 149:1299-1313 (1979).
Kitamura et al., "Targeted disruption of μ chain membrane exon causes loss of heavy-chain allelic exclusion," *Nature* 356:154-156 (1992).
Kozak, "An analysis of 5'-noncoding sequences from 699 vertebrate messenger RNAs," *Nucleic Acids Res* 15:8125-8148 (1987).
Lander et al., "Initial sequencing and analysis of the human genome," *Nature* 2001, 409:860-921 (2001).
Landsteiner et al., "On the Specificity of Serological Reactions with Simple Chemical Compounds (Inhibition Reactions)," *J Exp Med* 54:295-305 (1931).
Lefranc et al., "IMGT unique numbering for immunoglobulin and T cell receptor variable domains and Ig superfamily V-like domains," *Dev Comp Immunol* 27:55-77 (2003).
Lopez et al., "A single VH family and long CDR3s are the targets for hypermutation in bovine immunoglobulin heavy chains," *Immunol Rev* 162(1):55-66 (1998).
Lutz et al., "Pro-B cells sense productive immunoglobulin heavy chain rearrangement irrespective of polypeptide production," *Proc Nat Acad Sci USA* 108(26):10644-10649 (2011).
Mason et al., "Transcription cell type specificity is conferred by an immunoglobulin VH gene promoter that includes a functional consensus sequence," *Cell* 41:479-487 (1985).
Misra et al., "Gene targeting in the mouse: advances in introduction of transgenes into the genome by homologous recombination," *Endocrine* 19:229-238 (2002).

(56) References Cited

OTHER PUBLICATIONS

Mouse Genome Sequencing Consortium, "Initial sequencing and comparative analysis of the mouse genome," Nature 420:520-562 (2002).
Ristevski, "Making better transgenic models: conditional, temporal, and spatial approaches," Mol Biotechnol 29:153-163 (2005).
Roebroek et al., "Mutant Lrp1 knock-in mice generated by recombinase-mediated cassette exchange reveal differential importance of the NPXY motifs in the intracellular domain of LRP1 for normal fetal development," Mol Cell Biol 26:605-616 (2006).
Saiki et al., "Analysis of enzymatically amplified beta-globin and HLA-DQ alpha DNA with allele-specific oligonucleotide probes," Nature 324:163-166 (1986).
Schellenberg et al., "Pre-mRNA splicing: a complex picture in higher definition," Trends Biochem Sci 33:243-246 (2008).
Sharon, "The invariant tryptophan in an H chain V region is not essential to antibody binding," J Immunol 140:2666-2669 (1988).
Sinclair et al., "Bovine IgG repertoire is dominated by a single diversified VH gene family," J Immunol 159:3883-3889 (1997).
Tonegawa, "Somatic generation of antibody diversity," Nature 302:575-581 (1983).
Toor et al., "Structural insights into RNA splicing," Curr Opin Struct Biol 19:260-266 (2009).
Venter et al., "The sequence of the human genome," Science 291:1304-1351 (2001).
Von Heijne, "Protein targeting signals," Curr Opin Cell Biol 2:604-608 (1990).
Wang et al., "Reshaping Antibody Diversity," Cell 153:1379-1393 (2013).
Xiong et al., "Chemical gene synthesis: strategies, softwares, error corrections, and applications," FEMS Microbiol Rev 32:522-540 (2008).
Avitahl et al., "A 125 bp region of the Ig $V_H1$ promoter is sufficient to confer lymphocyte-specific expression in transgenic mice," Int Immunol 8(9):1359-1366 (1996).
Berman et al., "Content and organization of the human Ig $V_H$ locus: definition of three new $V_H$ families and linkage to the Ig $C_H$ locus," EMBO J 7(3):727-738 (1988).
Blankenstein et al., "Immunoglobulin $V_H$ region genes of the mouse are organized in overlapping cluster," Eur J Immunol 17:1351-1357 (1987).
Brekke et al., "Assembly and analysis of the mouse immunoglobulin kappa gene sequence," Immunogenetics 56:490-505 (2004).
Bruggemann, "The Preparation of Human Antibodies from Mice Harbouring Human Immunoglobulin Loci," Transgenic Animals: Generation and Use, pp. 397-402, Ed. L.M. Houdebine, CRC Press (1997).
Featherstone et al., "The Mouse Immunoglobulin Heavy Chain V-D Intergenic Sequence Contains Insulators That May Regulate Ordered V(D)J Recombination," J Biol Chem 285:9327-9338 (2010).
Ichihara et al., "Organization of human immunoglobulin heavy chain diversity gene loci," EMBO J 7(13):4141-4150 (1988).
Johnston et al., "Complete Sequence Assembly and Characterization of the C57BL/6 Mouse Ig Heavy Chain V Region," J Immunol 176:4221-4234 (2006).
Kawasaki et al., "One-Megabase Sequence Analysis of the Human Immunoglobulin λ Gene Locus," Genome Res 7:250-261 (1997).
Kurosawa et al., "Organization, Structure, and Assembly of Immunoglobulin Heavy Chain Diversity DNA Segments," J Exp Med 155:201-218 (1982).
Lee et al., "Genome data mining for everyone," BMB Reports 41(11):757-764 (2008).
Matsuda et al., "The Complete Nucleotide Sequence of the Human Immunoglobulin Heavy Chain Variable Region Locus," J Exp Med 188(11):2151-2162 (1998).
Sakano et al., "Identification and nucleotide sequence of a diversity DNA segment (D) of immunoglobulin heavy-chain genes," Nature 290:562-565 (1981).
Final Office Action in co-pending U.S. Appl. No. 13/818,184, dated Jun. 1, 2018.

Non-Final Office Action issued in U.S. Appl. No. 13/818,184, dated Mar. 8, 2019.
Gunasekaran et al., "Enhancing Antibody Fc Heterodimer Formation through Electrostatic Steering Effects," J Biol Chem 285:19637-19646 (2010).
Liu et al., "A Novel Antibody Engineering Strategy for Making Monovalent Bispecific Heterodimeric IgG Antibodies by Electrostatic Steering Mechanism," J Biol Chem 290:7535-7362 (2015).
Ma et al., "DNA Synthesis, Assembly and Applications in Synthetic Biology," Curr Opin Chem Biol 16:260-267 (2012).
Mclenachan et al., "Flow-cytometric analysis of mouse embryonic stem cell lipofection using small and large DNA constructs," Genomics 89:708-720 (2007).
Rajewsky et al., "Allelic exclusion model questioned," Scientific Correspondence, Nature 359:371-372 (1992).
Sonoda et al, "B Cell Development under the Condition of Allelic Inclusion," Immunity 6:225-233 (1997).
Vetterman et al., "Allelic exclusion of immunoglobulin genes: models and mechanisms," Immunol Rev 237:22-42 (2010).
Wabl et al., "Allelic exclusion model questioned," Scientific Correspondence, Nature 359:370-371 (1992).
Debono, et al., "Vh Gene Segments in the Mouse and Human Genomes", J. Mol. Biol., 342:131-34 (2004).
Wallace, et al., "Manipulating the Mouse Genome to Engineer Precise Functional Syntenic Replacements with Human Sequence", Cell, 128:197-209 (2007).
Zhang, et al., ":A New and Robust Method of Tethering IgG Surrogate Antigens on Lipid Bilayer Membranes to Facilitate the TIRFM Based Live Cell and Single Molecule Imaging Experiments", PLOS One, 8(5):e63735 (2013).
Clargo et al., "The rapid generation of recombinant functional monoclonal antibodies from individual, antigen-specific bone marrow-derived plasma cells isolated using a novel fluorescence-based method," mAbs 6(1): 143-159 (2013).
Li et al., "Biochemical Analysis of the Regulatory T Cell Protein Lymphocyte Activation Gene-3 (LAG-3; CD223)," Journal of Immunology 173: 6806-6812 (2004).
Manz et al., "Analysis and sorting of live cells according to secreted molecules relocated to a cell-surface affinity matrix," Proceedings of the National Academy of Science USA 92: 1921-1925 (1995).
Pinder et al., "Isolation and Characterization of Antigen-Specific Plasmablasts Using a Novel Flow Cytometry-Based Ig Capture Assay," Journal of Immunology 199(12): 4180-4188 (2017).
Price et al., "Engineered cell surface expression of membrane immunoglobulin as a means to identify monoclonal antibody-secreting hybridomas," Journal of Immunological Methods 343: 28-41 (2009).
Zhou et al., "Generation of Monoclonal Antibodies against Highly Conserved Antigens," PLoS One 4(6):e6087 (2009).
Non-final Office Action issued in U.S. Appl. No. 15/603,334, dated Aug. 22, 2019.
Brevini et al., "No shortcuts to pig embryonic stem cells," Theriogenology 74: 544-550 (2010).
Buta et al., "Reconsidering pluripotency tests: Do we sill need teratoma assays?" Stem Cell Research 11: 552-562 (2013).
Choe et al., "Fc-Binding Ligands of Immunoglobulin G: An Overview of High Affinity Proteins and Peptides," Materials 9: 994 (2016).
Gomez et al., "Derivation of cat embryonic stem-like cells from in vitro-produced blastocytes on homologous and heterologous feeder cells," Theriogenology 74: 498-515 (2010).
Ivics et al., "Germline transgenesis in rodents by pronuclear microinjection of Sleeping Beauty transposons," Nature Protocols 9(4); 773-793 (2014).
Kontermann et al., "Bispecific antibodies," Drug Discov Today 20(7):838-847 (2015).
Meng et al., "Optimized production of transgenic buffalo embryos and offspring by cytoplasmic zygote injection," Journal of Animal Science and Biotechnology 6: 44 (2015).
Munoz et al., "Conventional pluripotency markers are unspecific for bovine embryonic-derived cell-lines," Theriogenology 69: 1159-1164 (2008).

(56) References Cited

OTHER PUBLICATIONS

Paris et al., "Equine embryos and embryonic stem cells: Defining reliable markers of pluripotency," *Theriogenology* 74: 516-524 (2010).

Van Keuren et al., "Generating Transgenic Mice from Bacterial Artificial Chromosomes: Transgenesis Efficiency, Integration and Expression Outcomes," *Transgenic Research* 18(5): 769-785 (2009).

West et al., "Genome Editing in Large Animals," *Journal of Equine Veterinary Science* 41: 1-6 (2014).

\* cited by examiner

SEQUENCE LISTING

<160> NUMBER OF SEQ ID NOS: 13

<210> SEQ ID NO 1
<211> LENGTH: 100
<212> TYPE: DNA
<213> ORGANISM: Mus musculus

<400> SEQUENCE: 1
atttctgtac ctgatctatg tcaatatctg taccatggct ctagcagaga tgaaatatga    60
gacagtctga tgtcatgtgg ccatgcctgg tccagacttg                          100

<210> SEQ ID NO 2
<211> LENGTH: 100
<212> TYPE: DNA
<213> ORGANISM: Mus musculus

<400> SEQUENCE: 2

```
gtcaatcagc agaaatccat catacatgag acaaagttat aatcaagaaa tgttgcccat    60
aggaaacaga ggatatctct agcactcaga gactgagcac                         100
```

<210> SEQ ID NO 3
<211> LENGTH: 1103
<212> TYPE: DNA
<213> ORGANISM: Mus musculus

<400> SEQUENCE: 3

```
gcattgaata aaccagtata aacaagcaag caaagataga tagatagata gatagataga    60
tagatagata catagataga tagatagata gatgatgat agatagatag atagatagat   120
agattttttac gtataataca ataaaaacat tcattgtccc tctattggtg actactcaag  180
gaaaaaaatg ttcatatgca agaaaaaatg ttatcattac cagatgatcc agcaatctag  240
caatatatat attgtttatt cacaaaaacat gaatgaacct tttaagaagc tgttacagtg  300
taaaaattaa gttaaatcac tgaagaacat atactgtgtg atttcattca aatgaaattt  360
gagaagtaaa tatatatgta tatatatata tatgtaaaaa atataagtct gaactacaaa  420
aattcaattt gtttgatatg taagaataag aaaaattgac ccccaaaatt tgttaataat  480
taggtatgtg tatttttatg aatatataag tataataatg cttatagtat acactattct  540
gaatcacatt tattccctaa gtgtgttccc ttgattataa ttaaaagtat atttttaaa    600
tacagagtca gagtacagtc aataaggcga aaatatagtt gaatgatttg cttcagcttt  660
tgtaatgtac tagagattgt gagtacaaag tctcagagct catttatcc ctgacaataa   720
ccagctctgt gcttcaagta catttccatc tttctctgaa atttagtctt atatagatag  780
acaaaattta agtaaatttc aaactacaca gaacaactaa gttgttgttt catattgata  840
atggatttga actgcattaa cagaacttta acatcctgct tattctccct tcagccatca  900
tattttgctt tattatttc acttttgag ttatttttca cattcagaaa gctcacataa     960
ttgtcacttc tttgtatact ggtatacaga ccagaacatt tgcatattgt tccctgggga  1020
ggtcttttgcc ctgttggcct gagataaaac ctcaagtgtc ctcttgcctc cactgatcac  1080
tctcctatgt ttatttcctc aaa                                          1103
```

<210> SEQ ID NO 4
<211> LENGTH: 49
<212> TYPE: DNA
<213> ORGANISM: Bos taurus

<400> SEQUENCE: 4

```
atgagattct ctgctcagct cctggggctc ctcctgctct gggtcccag              49
```

<210> SEQ ID NO 5
<211> LENGTH: 401
<212> TYPE: DNA
<213> ORGANISM: Bos taurus

<400> SEQUENCE: 5

```
gtaagtacag agagggatga gaaggaggat gggggtgagt tctggggcag cactgctctc    60
cacatgtgtt ctctgttaga tgtgtatgac ttgtcctgca gatgagcatg ggaaccttag  120
atcaatgata gtgaggaatg ttccagaagg aagaaggtcc tgtgctctgg tcaggactgt  180
gacaggggaa gtggggatga tgtaggggat gtttagaggt ctcttttatac ttcacagata  240
tcaagttcat tattgtgatt gtacaatttt gctgtatgat cacagacaat gtgagtaata  300
```

```
caaagtagta ttaatgtttt agctaaaata aatcagaaaa tggaaacaat aaaaatggtt    360
gctaatattt gtagctttct aattctctgt cattccttta g                       401

<210> SEQ ID NO 6
<211> LENGTH: 308
<212> TYPE: DNA
<213> ORGANISM: Bos taurus

<400> SEQUENCE: 6
gatccagtgg ggatgttgtg ctgacccaga ctccactctc cctgtctatc atccctggag     60
agatggcctc catctcctgc aagtctagtc agagcctggt acacagtgat ggaaaaacct    120
atttgaattg gattcaatat aaaccaggcc aatcaccaca gggtctgatc tatcaggttt    180
ccaaccgtta ctctggggtc tcagacaggt tcactggcag tgggtcaggg acagatttca    240
cacttacaat cagcagagtg caggctgagg atgctggagt ctattactgt taccaaggta    300
cagaagat                                                             308

<210> SEQ ID NO 7
<211> LENGTH: 142
<212> TYPE: DNA
<213> ORGANISM: Mus musculus

<400> SEQUENCE: 7
atacagactc tatcaaaaac ttccttgcct ggggcagccc agctgacaat gtgcaatctg     60
aagaggagca gagagcatct tgtgtctgtg tgagaaggag gggctgggat acatgagtaa    120 ttcttttgcag ctgtgagctc tg                                            142

<210> SEQ ID NO 8
<211> LENGTH: 1103
<212> TYPE: DNA
<213> ORGANISM: Mus musculus

<400> SEQUENCE: 8
gcattgaata aaccagtata aacaagcaag caaagataga tagatagata gatagataga     60
tagatagata catagataga tagatagata gatagatgat agatagatag atagatagat    120
agatttttac gtataataca ataaaaacat tcattgtccc tctattggtg actactcaag    180
gaaaaaaatg ttcatatgca agaaaaaatg ttatcattac cagatgatcc agcaatctag    240
caatatatat attgtttatt cacaaaacat gaatgaacct tttaagaagc tgttacagtg    300
taaaaattaa gttaaatcac tgaagaacat atactgtgtg atttcattca aatgaaattt    360
gagaagtaaa tatatatgta tatatatata tatgtaaaaa atataagtct gaactacaaa    420
aattcaattt gtttgatatg taagaataag aaaaattgac ccccaaaatt tgttaataat    480
taggtatgtg tattttttatg aatatataag tataataatg cttatagtat acactattct    540
gaatcacatt tattccctaa gtgtgttccc ttgattataa ttaaaagtat atttttttaaa    600 tacagagtca gagtacagtc aataaggcga aaatatagtt gaatgatttg cttcagcttt    660
tgtaatgtac tagagattgt gagtacaaag tctcagagct catttttatcc ctgacaataa    720 ccagctctgt gcttcaagta catttccatc tttctctgaa atttagtctt atatagatag    780
acaaaattta agtaaatttc aaactacaca gaacaactaa gttgttgttt catattgata    840
atggatttga actgcattaa cagaacttta acatcctgct tattctcccct tcagccatca    900 tattttgctt tattattttc acttttttgag ttattttttca cattcagaaa gctcacataa    960
```

```
ttgtcacttc tttgtatact ggtatacaga ccagaacatt tgcatattgt tccctgggga    1020
ggtctttgcc ctgttggcct gagataaaac ctcaagtgtc ctcttgcctc cactgatcac    1080
tctcctatgt ttatttcctc aaa                                           1103

<210> SEQ ID NO 9
<211> LENGTH: 49
<212> TYPE: DNA
<213> ORGANISM: Mus musculus

<400> SEQUENCE: 9
atgatgagtc ctgcccagtt cctgtttctg ttagtgctct ggattcagg               49

<210> SEQ ID NO 10
<211> LENGTH: 386
<212> TYPE: DNA
<213> ORGANISM: Mus musculus

<400> SEQUENCE: 10
gtaaggagtt ttggaatgtg agggatgaga atggggatgg agggtgatct ctggatgcct    60
atgtgtgctg tttatttgtg gtggggcagg tcatatcttc cagaatgtga ggttttgtta   120
catcctaatg agatattcca catggaacag tatctgtact aagatcagta ttctgacata   180
gattggatgg agtggtatag actccatcta taatggatga tgtttagaaa cttcaacact   240
tgttttatga caaagcattt gatatataat attttttaaat ctgaaaaact gctaggatct   300
tacttgaaag gaatagcata aaagatttca caaaggttgc tcaggatctt tgcacatgat   360
tttccactat tgtattgtaa tttcag                                        386

<210> SEQ ID NO 11
<211> LENGTH: 11
<212> TYPE: DNA
<213> ORGANISM: Mus musculus

<400> SEQUENCE: 11
aaaccaacgg t                                                        11

<210> SEQ ID NO 12
<211> LENGTH: 308
<212> TYPE: DNA
<213> ORGANISM: Bos taurus

<400> SEQUENCE: 12
gatccagtgg ggatgttgtg ctgacccaga ctccactctc cctgtctatc atccctggag    60
agatggcctc catctcctgc aagtctagtc agagcctggt acacagtgat ggaaaaacct   120
atttgaattg gattcaatat aaaccaggcc aatcaccaca gggtctgatc tatcaggttt   180
ccaaccgtta ctctggggtc tcagacaggt tcactggcag tgggtcaggg acagatttca   240
cacttacaat cagcagagtg caggctgagg atgctggagt ctattactgt taccaaggta   300
cagaagat                                                            308

<210> SEQ ID NO 13
<211> LENGTH: 142
<212> TYPE: DNA
<213> ORGANISM: Mus musculus
```

```
<400> SEQUENCE: 13
atacagactc tatcaaaaac ttccttgcct ggggcagccc agctgacaat gtgcaatctg        60
aagaggagca gagagcatct tgtgtctgtg tgagaaggag gggctgggat acatgagtaa       120
ttctttgcag ctgtgagctc tg                                                142
```

TRANSGENIC MAMMALS AND METHODS OF USE THEREOF

CROSS-REFERENCE TO RELATED APPLICATIONS

This application is a continuation-in-part of U.S. Ser. No. 13/818,184 filed May 6, 2013, which is a § 371 filing of PCT/US2011/45333, filed Jul. 26, 2011, which claims priority to U.S. Provisional Patent Application No. 61/367,809, filed Jul. 26, 2010. This application also claims priority to U.S. Ser. No. 62/340,243, filed May 23, 2016, all of which are incorporated herein by reference.

FIELD OF THE INVENTION

This invention relates to production of immunoglobulin molecules, including methods for generating transgenic mammals capable of producing bovine antigen-specific antibody-secreting cells for the generation of monoclonal antibodies.

BACKGROUND OF THE INVENTION

In the following discussion certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Antibodies have emerged as important biological pharmaceuticals because they (i) exhibit exquisite binding properties that can target antigens of diverse molecular forms, (ii) are physiological molecules with desirable pharmacokinetics that make them well tolerated in treated humans and animals, and (iii) are associated with powerful immunological properties that naturally ward off infectious agents. Furthermore, established technologies exist for the rapid isolation of antibodies from laboratory animals, which can readily mount a specific antibody response against virtually any foreign substance not present natively in the body.

In their most elemental form, antibodies are composed of two identical heavy (H) chains that are each paired with an identical light (L) chain. The N-termini of both H and L chains consist of a variable domain ($V_H$ and $V_L$, respectively) that together provide the H-L paired with a unique antigen-binding specificity. The exons that encode the antibody $V_H$ and $V_L$ domains do not exist in the germ-line DNA. Instead, each $V_H$ exon is generated by the recombination of randomly selected V, D, and J gene segments present in the H chain locus (Igh; see schematic of the mouse Igh locus in FIG. 1); likewise, individual $V_L$ exons are produced by the chromosomal rearrangements of randomly selected V and J gene segments in a light chain locus. The bovine genome contains two alleles that can express the H chain (one allele from each parent), two alleles that can express the kappa (κ) L chain, and two alleles that can express the lambda (λ) L chain. There are multiple V, D, and J gene segments at the H chain locus as well as multiple V and J gene segments at both L chain loci. Downstream of the J gene segments at each immunoglobulin (Ig) locus exists one or more exons that encode the constant region of the antibody. In the heavy chain locus, exons for the expression of different antibody classes (isotypes) also exist. In bovine animals the encoded isotypes are IgM, IgD, IgG1, IgG2, IgG3, IgE, and IgA. Polymorphic variants (referred to as allotypes) also exist among bovine strains for all three IgG subclasses and are useful as allelic markers.

During B cell development, gene rearrangements occur first on one of the two homologous chromosomes that contain the H chain gene segments. The resultant $V_H$ exon is then spliced at the RNA level to the exons that encode the constant region of the H chain ($C_H$). Subsequently, the VJ rearrangements occur on one L chain allele at a time until a functional L chain is produced, after which the L chain polypeptides can associate with the H chain homodimers to form a fully functional B cell receptor for antigen (BCR).

The genes encoding various bovine (e.g., domestic cattle) and mouse immunoglobulins have been characterized, although the sequence and annotation of the bovine Ig loci in the genome databases is not yet complete. For example, Sinclair, et al., describe the bovine IgG repertoire as being dominated by a single diversified $V_H$ gene segment family in J. Immunol., 159(8):3883-89 (1997); Lopez, et al., describe a single $V_H$ family and long CDR3 as being the targets for hypermutation in bovine IgG heavy chains in Immunol. Rev. 162(1):55-66 (1998); Hosseini, et al., demonstrate that duplicated copies of the bovine $J_H$ locus contribute to the Ig repertoire in Int. Immunol. 16(6):355-63 (1998); Wang, et al., describe antigen-binding sites in certain bovine antibodies as ultralong CDR3 loops, each consisting of a stalk with a projecting knob that can be further somatically diversified by changing the number of Cys residues, as well as the patterns and connectivities of the somatically generated disulfide bonds in Cell, 153(6):1379-1393 (2013). Blankenstein and Krawinkel describe the mouse variable heavy chain region in Eur. J. Immunol. 17:1351-1357 (1987). The generation of transgenic animals—such as mice having varied immunoglobulin loci—has allowed the use of such transgenic animals in various research and development applications, e.g., in drug discovery and basic research into various biological systems. For example, the generation of transgenic mice bearing human immunoglobulin genes is described in International Application WO 90/10077 and WO 90/04036. WO 90/04036 describes a transgenic mouse with an integrated human immunoglobulin "mini" locus. WO 90/10077 describes a vector containing the immunoglobulin dominant control region for use in generating transgenic animals.

Numerous methods have been developed for modifying mouse endogenous immunoglobulin variable region gene locus with, e.g., human immunoglobulin sequences to create partially or fully human antibodies for drug discovery purposes. Examples of such mice include those described in, e.g., U.S. Pat. Nos. 7,145,056; 7,064,244; 7,041,871; 6,673,986; 6,596,541; 6,570,061; 6,162,963; 6,130,364; 6,091,001; 6,023,010; 5,593,598; 5,877,397; 5,874,299; 5,814,318; 5,789,650; 5,661,016; 5,612,205; and 5,591,669. However, many of the fully humanized immunoglobulin transgenic mice exhibit suboptimal antibody production because B cell development in these mice is severely hampered by inefficient V(D)J recombination, and by inability of the fully human antibodies/BCRs to function optimally with mouse signaling proteins. Other humanized immunoglobulin transgenic mice in which the mouse coding sequences have been "swapped" with human sequences are very time consuming and expensive to create due to the approach of replacing individual mouse exons with the syntenic human counterpart.

The use of antibodies that function as drugs is not necessarily limited to the prevention or therapy of human disease. In animal husbandry, there is increasing pressure to reduce or eliminate the use of antibiotics. As it is, the massive use of antibiotics favors the outgrowth of resistant microbes, endangering both farm animals and the humans who consume them. Based on the foregoing, it is clear that a need exists for efficient and cost-effective methods to produce bovine antibodies for the treatment of diseases in domestic cattle. More particularly, there is a need in the art for small, rapidly breeding mammals capable of producing antigen-specific bovine immunoglobulins. Preferentially, these non-bovine mammals will be useful for generating hybridomas capable of large-scale production of bovine monoclonal antibodies.

In accordance with the foregoing object, transgenic non-human animals are provided which are capable of producing an antibody with bovine V regions.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention comprises a non-bovine mammalian cell and a non-bovine mammal having a genome comprising an exogenously introduced, partly bovine immunoglobulin locus, where the introduced locus comprises coding sequences of the bovine immunoglobulin variable region genes and non-coding sequences based on the endogenous immunoglobulin variable gene locus of the non-bovine mammalian host. Thus, the non-bovine mammalian cell or mammal of the invention is capable of expressing a chimeric BCR or antibody comprising H and L chain variable regions that are fully bovine in conjunction with the respective constant regions that are native to the non-bovine mammalian host cell or mammal. Preferably, the transgenic cells and animals of the invention have genomes in which part or all of the endogenous immunoglobulin variable region gene locus is removed.

At a minimum, the production of chimeric bovine monoclonal antibodies in a non-bovine mammalian host requires the host to have at least one locus that expresses a chimeric bovine immunoglobulin H or L chain. In most aspects, there are one heavy chain locus and two light chain loci that, respectively, express chimeric bovine immunoglobulin H and L chains.

In some aspects, the partly bovine immunoglobulin locus comprises bovine $V_H$ coding sequences and non-coding regulatory or scaffold sequences present in the endogenous $V_H$ gene locus of the non-bovine mammalian host. In these aspects, the partly bovine immunoglobulin locus further comprises bovine $D_H$ and $J_H$ gene segment coding sequences in conjunction with the non-coding regulatory or scaffold sequences present in the vicinity of the endogenous $D_H$ and $J_H$ gene segments of the non-bovine mammalian host cell genome.

In other aspects, the partly bovine immunoglobulin locus comprises bovine $V_L$ coding sequences and non-coding regulatory or scaffold sequences present in the endogenous $V_L$ gene locus of the non-bovine mammalian host. More preferably, the exogenously introduced, partly bovine immunoglobulin locus comprising bovine $V_L$ coding sequences further comprises bovine L chain J gene coding sequences and non-coding regulatory or scaffold sequences present in the vicinity of the endogenous L chain J gene segments of the non-bovine mammalian host cell genome.

In certain aspects, the non-bovine mammal is a rodent, preferably, a mouse or rat.

In one specific aspect, the invention provides a method for generating a non-bovine mammalian cell comprising a partly bovine immunoglobulin locus, said method comprising: a) introducing two or more recombinase-targeting sites into the genome of a non-bovine mammalian host cell and integrating at least one site upstream and at least one site downstream of a genomic region comprising endogenous immunoglobulin variable region genes; and b) introducing into the non-bovine mammalian host cell via recombinase-mediated cassette exchange (RMCE) an engineered, partly bovine immunoglobulin variable gene locus comprising bovine immunoglobulin variable region gene coding sequences and non-coding sequences corresponding to the non-coding sequences present in the endogenous immunoglobulin variable region gene locus of the non-bovine mammalian host cell genome.

In another aspect, the method further comprises deleting the genomic region flanked by the two exogenously introduced recombinase-targeting sites prior to step b).

In a specific aspect of this method, the exogenously introduced, engineered, partly bovine immunoglobulin locus comprises bovine $V_H$ gene segment coding sequences, and further comprises i) bovine $D_H$ and $J_H$ gene segment coding sequences and ii) non-coding regulatory or scaffold sequences upstream of the bovine $D_H$ gene segments (pre-D sequences, FIG. 1) that correspond to the sequences present upstream of the endogenous $D_H$ gene segments in the genome of the non-bovine mammalian host. Furthermore, these upstream sequences may contain non-immunoglobulin genes, such as ADAM6 (FIG. 1) needed for male fertility (Nishimura et al. Developmental Biol. 233(1): 204-213 (2011)). The partly bovine immunoglobulin locus is introduced into the host cell using recombinase-targeting sites that have been previously introduced upstream of the endogenous immunoglobulin $V_H$ gene locus and downstream of the endogenous $J_H$ gene locus on the same chromosome.

In other aspects, the non-coding regulatory or scaffold sequences derive (at least partially) from other sources— e.g., they could be rationally or otherwise designed sequences, sequences that are a combination of bovine and other designed sequences, or sequences from other species.

In yet another specific aspect of the method, the introduced, engineered, partly bovine immunoglobulin locus comprises bovine immunoglobulin $V_L$ gene coding sequences, and further comprises i) bovine L chain J gene coding sequences and ii) non-coding regulatory or scaffold sequences corresponding to the non-coding regulatory or scaffold sequences present in the endogenous L chain locus of the non-bovine mammalian host cell genome. The engineered, partly bovine immunoglobulin locus is preferably introduced into the host cell using recombinase-targeting sites that have been previously introduced upstream of the endogenous immunoglobulin $V_L$ genes and downstream of the endogenous J gene locus on the same chromosome.

Preferably, the engineered, partly bovine immunoglobulin locus is synthesized as a single nucleic acid, and introduced into the non-bovine mammalian host cell as a single nucleic acid region. The engineered, partly bovine immunoglobulin locus may also be synthesized in two or more contiguous segments, and introduced to the mammalian host cell as discrete segments. The engineered, partly bovine immunoglobulin locus can also be produced using recombinant methods and isolated prior to being introduced into the non-bovine mammalian host cell.

In another aspect, the invention provides methods for generating a non-bovine mammalian cell comprising an engineered, partly bovine immunoglobulin locus, said method comprising: a) introducing into the genome of a non-bovine mammalian host cell two or more sequence-specific recombination sites that are not capable of recombining with one another, wherein at least one recombination site is introduced upstream of an endogenous immunoglobulin variable region gene locus while at least one recombination site is introduced downstream of the endogenous immunoglobulin variable region gene locus on the same chromosome; b) providing a vector comprising an engineered, partly bovine immunoglobulin locus having i) bovine immunoglobulin variable region gene coding sequences and ii) non-coding regulatory or scaffold sequences based on an endogenous immunoglobulin variable region gene locus of the host cell genome, wherein the partly bovine immunoglobulin locus is flanked by the same two sequence-specific recombination sites that flank the endogenous immunoglobulin variable region gene locus of the host cell of a); c) introducing into the host cell the vector of step b) and a site-specific recombinase capable of recognizing the two recombinase sites; d) allowing a recombination event to occur between the genome of the cell of a) and the partly bovine immunoglobulin locus, resulting in a replacement of the endogenous immunoglobulin variable region gene locus with the engineered, partly bovine immunoglobulin variable region gene locus. In a specific aspect of this method, the partly bovine immunoglobulin locus comprises $V_H$ immunoglobulin gene coding sequences, and further comprises i) bovine $D_H$ and $J_H$ gene segment coding sequences, ii) non-coding regulatory or scaffold sequences surrounding the codons of individual $V_H$, $D_H$, and $J_H$ gene segments present endogenously in the genome of the non-bovine mammalian host cell, and iii) pre-D sequences based on the endogenous genome of the non-bovine mammalian host cell. The recombinase-targeting sites are introduced upstream of the endogenous immunoglobulin $V_H$ gene locus and downstream of the endogenous $D_H$ and $J_H$ gene loci.

Thus, in some embodiments, there is provided a transgenic rodent with a genome deleted of a rodent endogenous immunoglobulin variable gene locus and replaced with endogenous immunoglobulin variable gene locus has been inserted an engineered partly bovine immunoglobulin locus comprising bovine immunoglobulin variable gene coding sequences and non-coding regulatory sequences based on the rodent endogenous immunoglobulin variable gene locus, wherein the engineered partly bovine immunoglobulin locus of the transgenic rodent is functional and expresses immunoglobulin chains comprised of bovine variable domains and rodent constant domains. In some aspects, the engineered partly bovine immunoglobulin locus comprises bovine $V_H$, $D_H$, and $J_H$ coding sequences, and in some aspects, the engineered partly bovine immunoglobulin locus comprises bovine $V_H$, $D_H$, $J_H$, or $V_L$ and $J_L$ coding sequences. Some aspects provide a cell of B lymphocyte lineage from the transgenic rodent, a part or whole immunoglobulin molecule comprising bovine variable domains and rodent constant domains derived from the cell of B lymphocyte lineage, a hybridoma cell derived from the cell of B lymphocyte, a part or whole immunoglobulin molecule comprising bovine variable domains and rodent constant domains derived from the hybridoma cell, an immortalized cell derived from the cell of B lymphocyte lineage, a part or whole immunoglobulin molecule comprising bovine variable domains and rodent constant domains derived from the immortalized cell. Other aspects of the invention provide a transgenic rodent, wherein the engineered partly bovine immunoglobulin locus comprises bovine $V_L$ and $J_L$ coding sequences, and a transgenic rodent, wherein the engineered partly bovine immunoglobulin locus comprises bovine $V_H$, $D_H$, $J_H$, or $V_L$ and $J_L$ coding sequences. In some aspects, the rodent is a mouse. In some aspects, the non-coding regulatory sequences comprise a promoter that precedes individual V gene segments, splice sites, and recombination signal sequences for promoting V(D)J recombination, and in other aspects the engineered partly bovine immunoglobulin locus further comprises one or more of an ADAM6 gene, a Pax-5-Activated Intergenic Repeat (PAIR) elements, or CTCF binding sites from a heavy chain intergenic control region 1.

Preferably, the non-bovine mammalian cell for use in each of the above methods is a mammalian cell, and more preferably a mammalian embryonic stem (ES) cell.

Once the cells have been subjected to the replacement of the endogenous immunoglobulin variable region gene locus by the introduced, partly bovine immunoglobulin variable region gene locus, the cells are selected and preferably isolated. In a preferred aspect of the invention, the cells are non-bovine mammalian ES cells, preferably rodent embryonic stem cells, and at least one isolated ES cell clone is then utilized to create a transgenic non-bovine mammal expressing the engineered, partly bovine immunoglobulin variable region gene locus.

An embodiment of the invention provides a method for generating the transgenic rodent, said method comprising: integrating into a rodent cell's genome at least one target site for a site-specific recombinase in a rodent cell's genome upstream of an endogenous immunoglobulin variable gene locus and at least one target site for a site-specific recombinase downstream of the endogenous immunoglobulin variable gene locus, wherein the endogenous immunoglobulin variable locus comprises $V_H$, $D_H$ and $J_H$ gene segments, or $V_\kappa$ and $J_\kappa$ gene segments, or $V_\lambda$ and $J_\lambda$ gene segments, or $V_\lambda$, $J_\lambda$ and $C_\lambda$ gene segments; providing a vector comprising an engineered partly bovine immunoglobulin locus, said engineered partly bovine immunoglobulin locus comprising partly bovine immunoglobulin gene segments, wherein each of the partly bovine immunoglobulin gene segment comprises bovine immunoglobulin variable gene coding sequences and rodent non-coding regulatory sequences, with the partly bovine immunoglobulin gene segments being flanked by target sites for a site-specific recombinase wherein the target sites are capable of recombining with the target sites introduced into the rodent cell; introducing into the cell the vector and a site-specific recombinase capable of recognizing the target sites; allowing a recombination event to occur between the genome of the cell and the engineered partly bovine immunoglobulin locus resulting in a replacement of the endogenous immunoglobulin variable gene locus with the engineered partly bovine immunoglobulin locus; selecting a cell that comprises the engineered partly bovine immunoglobulin variable locus generated in step d); and utilizing the cell to create a transgenic rodent comprising partly bovine the engineered partly bovine immunoglobulin variable locus. In some aspects, the cell is a rodent embryonic stem (ES) cell, and in some aspects the cell is a mouse embryonic stem (ES) cell. Some aspects of this method further comprise after the introducing step and before the providing step a step of deleting the endogenous immunoglobulin variable gene locus by introduction of a recombinase that recognizes a first set of target sites, wherein the deleting step leaves in place a second set of target sites in the rodent cell's genome, where the second set of target sites are not capable of recombining with one another. In some aspects, the vector comprises bovine $V_H$, $D_H$, and $J_H$, coding sequences, and in some aspects the vector comprises bovine $V_L$ and $J_L$ coding sequences. In some aspects, the vector further comprises a promoter, splice sites, and recombination signal sequences.

In another aspect, the invention provides a method for generating a transgenic non-bovine mammal comprising an exogenously introduced, engineered, partly bovine immunoglobulin variable region gene locus, said method comprising: a) introducing into the genome of a non-bovine mammalian host cell one or more sequence-specific recombination sites that flank an endogenous immunoglobulin variable region gene locus and are not capable of recombining with one another; b) providing a vector comprising a partly bovine immunoglobulin locus having i) bovine variable region gene coding sequences and ii) non-coding regulatory or scaffold sequences based on the endogenous (e.g., rodent) immunoglobulin variable region gene locus, wherein the coding and non-coding sequences are flanked by the same sequence-specific recombination sites as those introduced to the genome of the host cell of a); c) introducing into the cell the vector of step b) and a site-specific recombinase capable of recognizing one set of recombinase sites; d) allowing a recombination event to occur between the genome of the cell of a) and the engineered, partly bovine immunoglobulin variable region gene locus, resulting in a replacement of the endogenous immunoglobulin variable region gene locus with the partly bovine immunoglobulin locus; e) selecting a cell which comprises the partly bovine immunoglobulin locus; and f) utilizing the cell to create a transgenic animal comprising the partly bovine immunoglobulin locus.

In a specific aspect, the engineered, partly bovine immunoglobulin locus comprises bovine $V_H$, $D_H$ and $J_H$ gene segment coding sequences, and non-coding pre-D sequences (including fertility enabling gene) present in the endogenous genome of the non-bovine mammalian host. The sequence-specific recombination sites are then introduced upstream of the endogenous immunoglobulin $V_H$ gene segments and downstream of the endogenous immunoglobulin $J_H$ gene segments.

The invention provides another method for generating a transgenic non-bovine animal comprising an engineered, partly bovine immunoglobulin locus, said method comprising: a) providing a non-bovine mammalian cell having a genome that comprises two sets of sequence-specific recombination sites that are not capable of recombining with one another, and which flank a portion of an endogenous immunoglobulin variable region gene locus of the host genome; b) deleting the portion of the endogenous immunoglobulin locus of the host genome by introduction of a recombinase that recognizes a first set of sequence-specific recombination sites, wherein such deletion in the genome retains the second set of sequence-specific recombination sites; c) providing a vector comprising an engineered, partly bovine immunoglobulin variable region gene locus having bovine coding sequences and non-coding regulatory or scaffold sequences based on the endogenous immunoglobulin variable region gene locus, where the coding and non-coding sequences are flanked by the second set of sequence-specific recombination sites; d) introducing the vector of step c) and a site-specific recombinase capable of recognizing the second set of sequence-specific recombination sites into the cell; e) allowing a recombination event to occur between the genome of the cell and the engineered, partly bovine immunoglobulin locus, resulting in a replacement of the endogenous immunoglobulin locus with the engineered, partly bovine immunoglobulin locus; f) selecting a cell that comprises the partly bovine immunoglobulin variable region gene locus; and g) utilizing the cell to create a transgenic animal comprising the engineered, partly bovine immunoglobulin variable region gene locus.

The invention provides yet another method for generating a transgenic non-bovine mammal comprising an engineered, partly bovine immunoglobulin locus, said method comprising: a) providing a non-bovine mammalian ES cell having a genome that contains two sequence-specific recombination sites that are not capable of recombining with each other, and which flank the endogenous immunoglobulin variable region gene locus; b) providing a vector comprising an engineered, partly bovine immunoglobulin locus comprising bovine immunoglobulin variable gene coding sequences and non-coding regulatory or scaffold sequences based on the endogenous immunoglobulin variable gene locus, where the partly bovine immunoglobulin locus is flanked by the same two sequence-specific recombination sites that flank the endogenous immunoglobulin variable region gene locus in the ES cell; c) bringing the ES cell and the vector into contact with a site-specific recombinase capable of recognizing the two recombinase sites under appropriate conditions to promote a recombination event resulting in the replacement of the endogenous immunoglobulin variable region gene locus with the engineered, partly bovine immunoglobulin variable region gene locus in the ES cell; d) selecting an ES cell that comprises the engineered partly bovine immunoglobulin locus; and e) utilizing the cell to create a transgenic animal comprising the engineered, partly bovine immunoglobulin locus.

In a specific aspect of the invention, the transgenic non-bovine mammal is a rodent, e.g., a mouse or a rat.

The invention further provides a non-bovine mammalian cell and a non-bovine transgenic mammal expressing an introduced immunoglobulin variable region gene locus having bovine immunoglobulin variable region gene coding sequences and non-coding sequences based on the endogenous non-bovine immunoglobulin locus of the host genome, where the non-bovine mammalian cell and transgenic animal expresses chimeric antibodies consisting of fully bovine H and/or L chain variable domains in conjunction with their respective constant regions that are native to the non-bovine mammalian cell or animal.

Further, the invention also provides B cells from a transgenic animal that are capable of expressing partly bovine antibodies having bovine variable sequences, wherein such B cells are immortalized to provide sources of monoclonal antibodies specific for a particular antigen.

The invention additionally provides bovine immunoglobulin variable region gene sequences cloned from B cells for use in the production and/or optimization of antibodies for diagnostic, preventive, or therapeutic uses.

Also, the invention provides hybridoma cells that are capable of producing partly bovine monoclonal antibodies having bovine immunoglobulin variable region sequences.

The invention also provides methods for removing the $V_H$ and $V_L$ exons that encode the H and L chain immunoglobulin variable domains from the monoclonal antibody-producing hybridomas and reconfiguring them to contain bovine constant regions, thereby creating a fully bovine antibody that is not immunogenic when injected into cattle.

These and other aspects, objects and features are described in more detail.

DEFINITIONS

Figure 1:
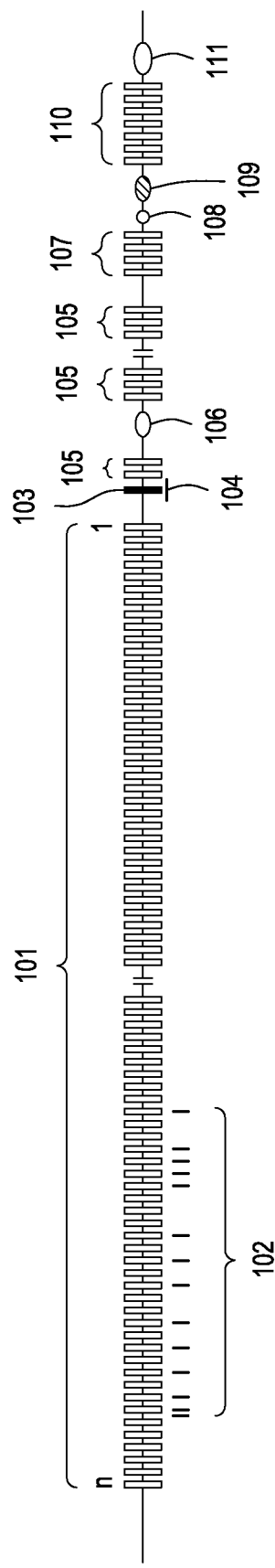
FIG. 1 is a schematic diagram of the endogenous mouse Igh locus located at the telomeric end of chromosome 12.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "locus" as used herein refers to a chromosomal segment or nucleic acid sequence that, respectively, is present endogenously in the genome or is (or about to be) exogenously introduced into the genome. For example, an immunoglobulin locus may include part or all of the genes (i.e., V, D, J gene segments as well as constant region genes) and intervening sequences (i.e., introns, enhancers, etc.) supporting the expression of immunoglobulin H or L chain polypeptides. Thus, a locus (e.g., $V_H$ gene locus) may refer to a specific portion of a larger locus (e.g., immunoglobulin H chain locus).

The term "immunoglobulin variable region gene" as used herein refers to a V, D, or J gene segment that encodes a portion of an immunoglobulin H or L chain variable domain. The term "immunoglobulin variable region gene locus" as used herein refers to part of, or the entire, chromosomal segment or nucleic acid strand containing clusters of the V, D, or J gene segments and may include the non-coding regulatory or scaffold sequences.

"Partly bovine" as used herein refers to a strand of nucleic acids, or their expressed protein and RNA products, comprising sequences corresponding to the sequences found in a given locus of both a bovine and a non-bovine mammalian host. "Partly bovine" as used herein also refers to an animal comprising nucleic acid sequences from both a bovine and a non-bovine mammal, preferably a rodent. In the context of partly bovine sequences of the invention, the partly bovine nucleic acids have coding sequences of bovine immunoglobulin H or L chain variable region gene segments and sequences based on the non-coding regulatory or scaffold sequences of the endogenous immunoglobulin locus of the non-bovine mammal. The term "based on" when used with reference to the endogenous non-coding regulatory or scaffold sequences from a non-bovine mammalian host cell genome refers to the non-coding regulatory or scaffold sequences that are present in the corresponding endogenous locus of the mammalian host cell genome. Non-coding "regulatory sequences" refer to sequences that are known to be essential for (i) V(D)J recombination, (ii) isotype switching, and (iii) proper expression of the full-length immunoglobulin H or L chains following V(D)J recombination. "Non-coding regulatory sequences" may further include the following sequences of endogenous origin: enhancer and locus control elements such as the CTCF and PAIR sequences (Proudhon, et al., Adv. Immunol. 128:123-182 (2015)); promoters preceding each endogenous V gene segment; splice sites; introns; recombination signal sequences flanking each V, D, or J gene segment. Preferably, the "non-coding regulatory sequences" of the partly bovine immunoglobulin locus share at least 70% homology with the corresponding non-coding sequences found in the targeted endogenous immunoglobulin locus of the non-bovine mammalian host cell. "Scaffold sequences" refer to non-immunoglobulin genes, such as ADAM6, and other sequences with unknown functions present in the endogenous immunoglobulin locus of the host cell genome. In certain aspects, the non-coding regulatory or scaffold sequences are derived (at least partially) from other sources—e.g., they could be rationally or otherwise designed sequences, sequences that are a combination of bovine and other designed sequences, or sequences from other species. It is to be understood that the phrase "non-coding regulatory or scaffold sequence" is inclusive in meaning (i.e., referring to both the non-coding regulatory sequence and the scaffold sequence existing in a given locus).

The term "homology targeting vector" refers to a nucleic acid sequence used to modify the endogenous genome of a mammalian host cell by homologous recombination; such nucleic acid sequence may comprise (i) targeting sequences with significant homologies to the corresponding endogenous sequences flanking a locus to be modified that is present in the genome of the non-bovine mammalian host, (ii) at least one sequence-specific recombination site, (iii) non-coding regulatory or scaffold sequences, and (iv)

optionally one or more selectable marker genes. As such, a homology targeting vector can be used in the present invention to introduce a sequence-specific recombination site into particular region of a host cell genome.

"Site-specific recombination" refers to a process of DNA rearrangement between two compatible recombination sequences including any of the following three events: a) deletion of a preselected nucleic acid flanked by the recombination sites; b) inversion of the nucleotide sequence of a preselected nucleic acid flanked by the recombination sites, and c) reciprocal exchange of nucleic acid sequences proximate to recombination sites located on different nucleic acid strands. It is to be understood that this reciprocal exchange of nucleic acid segments can be exploited as a targeting strategy to introduce an exogenous nucleic acid sequence into the genome of a host cell.

The term "targeting sequence" refers to a sequence homologous to DNA sequences in the genome of a cell that flank or are adjacent to the region of an immunoglobulin locus to be modified. The flanking or adjacent sequence may be within the locus itself or upstream or downstream of coding sequences in the genome of the host cell. Targeting sequences are inserted into recombinant DNA vectors which are used to transfect e.g., ES cells, such that sequences to be inserted into the host cell genome, such as the sequence of a recombination site, are flanked by the targeting sequences of the vector.

The term "site-specific targeting vector" as used herein refers to a vector comprising a nucleic acid encoding a sequence-specific recombination site; an engineered, partly bovine locus; and optionally a selectable marker gene, which is used to modify an endogenous immunoglobulin locus in a host using recombinase-mediated site-specific recombination. The recombination site of the targeting vector is suitable for site-specific recombination with another corresponding recombination site that has been inserted into a genomic sequence of the host cell (e.g., via a homology targeting vector), adjacent to an immunoglobulin locus which is to be modified. Integration of an engineered, partly bovine sequence into a recombination site in an immunoglobulin locus results in replacement of the endogenous locus by the exogenously introduced, partly bovine sequence.

The term "transgene" is used herein to describe genetic material that has been or is about to be artificially inserted into the genome of a cell, and particularly a cell of a mammalian host animal. The term "transgene" as used herein refers to a partly bovine nucleic acid, e.g., a partly bovine nucleic acid in the form of an engineered expression construct and/or a targeting vector.

"Transgenic animal" refers to a non-bovine animal, usually a mammal, having an exogenous nucleic acid sequence present as an extrachromosomal element in a portion of its cells or stably integrated into its germ line DNA (i.e., in the genomic sequence of most or all of its cells). In the present invention, a partly bovine nucleic acid is introduced into the germ line of such transgenic animals by genetic manipulation of, for example, embryos or embryonic stem cells of the host animal according to methods well known in the art.

A "vector" includes plasmids and viruses and any DNA or RNA molecule, whether self-replicating or not, which can be used to transform or transfect a cell.

DETAILED DESCRIPTION OF THE INVENTION

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), Genome Analysis: A Laboratory Manual Series (Vols. I-IV); Weiner, Gabriel, Stephens, Eds. (2007), Genetic Variation: A Laboratory Manual; Dieffenbach and Veksler Eds. (2007), PCR Primer: A Laboratory Manual; Bowtell and Sambrook (2003), DNA Microarrays: A Molecular Cloning Manual; Mount (2004), Bioinformatics: Sequence and Genome Analysis; Sambrook and Russell (2006), Condensed Protocols from Molecular Cloning: A Laboratory Manual; and Sambrook and Russell (2002), Molecular Cloning: A Laboratory Manual (all from Cold Spring Harbor Laboratory Press); Stryer, L. (1995) Biochemistry (4th Ed.) W.H. Freeman, New York N.Y.; Gait, "Oligonucleotide Synthesis: A Practical Approach" 1984, IRL Press, London; Nelson and Cox (2000), Lehninger, Principles of Biochemistry 3.sup.rd Ed., W. H. Freeman Pub., New York, N.Y.; and Berg et al. (2002) Biochemistry, 5.sup.th Ed., W.H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a locus" refers to one or more loci, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

In the humoral immune system, a diverse antibody repertoire is produced by combinatorial and junctional diversity of IgH (Igh) and IgL chain (Igl) gene loci by a process termed V(D)J recombination. In the developing B cell, the first recombination event to occur is between one D and one J gene segment of the heavy chain locus, and the DNA between these two gene segments is deleted. This D-J recombination is followed by the joining of one V gene segment from a region upstream of the newly formed DJ complex, forming a rearranged VDJ exon. All other sequences between the recombined V and D gene segments of the newly generated VDJ exon are deleted from the genome of the individual B cell. This rearranged exon is ultimately expressed on the B cell surface as the variable region of the H chain polypeptide, which is associated with an L chain polypeptide to form the B cell receptor (BCR). The murine and bovine immunoglobulin loci are highly complex in the numbers of features they contain and in how their coding regions are diversified by V(D)J rearrangement; however, this complexity does not extend to the basic details of the structure of each variable region gene segment. The V, D and J gene segments are highly uniform in their compositions and organizations. For example, V gene segments have the following features that are arranged in essentially invariant sequential fashion in immunoglobulin loci: a short transcriptional promoter region (<600 bp in length), an exon encoding the majority of the signal peptide for the antibody chain, an intron, an exon encoding a small part of the signal peptide of the antibody chain and the majority of the antibody variable domain, and a 3' recombination signal sequence necessary for V(D)J rearrangement. Similarly, D gene segments have the following necessary and invariant features: a 5' recombination signal sequence, a coding region, and a 3' recombination signal sequence; and J gene segments have the following necessary and invariant features: a 5' recombination signal sequence, a coding region, and a 3' splice donor sequence.

The present invention provides non-bovine mammalian cells comprising an exogenously introduced, engineered, partly bovine nucleic acid sequence comprising coding sequences for bovine variable regions and non-coding sequences (e.g., promoter, 5' and 3' recombination sequences, and splice acceptor site) present in the immunoglobulin locus of the mammalian host genome, e.g., mouse genomic non-coding sequences when the host mammal is a mouse. Compared with humans and mice, cattle have fewer germline heavy chain V, D and J segments. Only a single $V_H$ family, designated as $BoV_H1$, is expressed at the cDNA level, and it is thought that the bovine genome contains about 20 $V_H$ gene segments based on the currently available data. Only ten $D_H$ and four functional $J_H$ gene segments have been identified. Nevertheless, the bovine $D_H$ segments can be long. One bovine $D_H$ (termed $D_H2$) consists of 149 nucleotides, accounting for 49 amino acid codons. This long $D_H$ contributes significantly to the length of the complementarity-determining region 3 (CDR3) of the bovine immunoglobulin H chain. By comparison, the average H chain CDR3 length in mice is ~11 amino acids and in humans is ~15 amino acids. Thus, bovine antibodies are of two types, conventional antibodies, albeit with comparatively longer CDR3s (~25 amino acids), and those with ultralong CDR3s, which range from 40-67 residues, with an average of ~58 amino acids. The exceptionally long CDR3 has a unique structure; it is composed of a supporting stalk with a projecting knob. In conventional antibodies the CDR loops of both H and L chain variable regions can contribute to antigen binding. However, in the ultralong (UL) CDR3 antibodies the CDR H1, H2, L1, and L2 loops only form the supporting stalk, and the UL CDR H3 loop forms the knob structure, which binds antigen and can be enormously diversified by changing the number of Cys residues as well as the resulting patterns and connectivities of the somatically generated disulfide bonds. The heavy chains of all UL bovine antibodies analyzed to date are encoded by a single $V_H$ gene segment, VHBUL, a single $D_H$ gene segment, $D_H2$, and a single $J_H$ gene segment, $J_H1$. Similar to humans and mice, two types of Ig light chains (κ and λ) are expressed in cattle, though the λ to κ ratio differs significantly among these animals. In mice, approximately 96% of light chains in the serum antibodies are the κ type, while the κ type in humans accounts for only 66% of the total population of IgL chains. In contrast, the L chain repertoire in cattle is dominated by λ chains. Cattle have 20 functional Vλ and 8 functional Vκ genes. However, the UL bovine antibodies use a single Vλ, Vλ1x.

The present invention comprises the use of a synthetic or recombinantly produced, engineered, partly bovine nucleic acids comprising both bovine coding sequences and non-bovine non-coding sequences from an immunoglobulin $V_H$, Vλ, or Vκ locus, or a combination thereof.

In an aspect of the invention, the synthetic H chain DNA segment contains the ADAM6 gene needed for male fertility, Pax-5-Activated Intergenic Repeats (PAIR) elements involved in Igh locus contraction, and CTCF binding sites from the heavy chain intergenic control region 1, involved in regulating normal VDJ rearrangement (Proudhon, et al., Adv. Immunol. 128:123-182 (2015)), or various combinations thereof. The locations of these endogenous non-coding regulatory and scaffold sequences in the mouse Igh locus are depicted in FIG. 1, which illustrates from left to right: the 113 functional heavy chain variable region gene segments (101); PAIR, Pax-5 Activated Intergenic Repeats involved in Igh locus contraction for VDJ recombination (102); Adam6a, a disintegrin and metallopeptidase domain 6A gene required for male fertility (103); Pre-D region, a 21609 bp fragment upstream of the most distal $D_H$ gene segment, Ighd-5 $D_H$ (104); Intergenic Control Region 1 (IGCR1) that contains CTCF insulator sites to regulate $V_H$ gene segment usage (106); $D_H$, diversity gene segments (10-15 depending on the mouse strain) (105); four joining $J_H$ gene segments (107); Eμ, the intronic enhancer involved in VDJ recombination and heavy chain expression (108); Sp., the μ switch region for isotype switching (109); eight heavy chain constant region genes: Cμ, Cδ, Cγ3, Cγ1, Cγ2b, C2γa/c, Cε, and Cα (110); 3' Regulatory Region (3'RR) that controls isotype switching and somatic hypermutation (111). FIG. 1 is a modified version of a Figure taken from Proudhon et al. (2015).

In preferred aspects of the invention, the engineered, partly bovine immunoglobulin locus to be introduced into a mammalian host cell comprises all or a substantial number of the known bovine $V_H$ gene segments. In some instances, however, it may be desirable to use a subset of such $V_H$ gene segments, and in specific instances even as few as one bovine $V_H$ coding sequence may be introduced into the cell or the animal of the invention.

The preferred aspects of the invention comprise non-bovine mammals and mammalian cells comprising an engineered, partly bovine immunoglobulin locus that comprises coding sequences of bovine $V_H$, bovine $D_H$, and bovine $J_H$ gene segments, and that further comprises non-coding sequences, including pre-D sequences, based on the endogenous Igh locus of the non-bovine mammalian host. In certain aspects, the exogenously introduced, engineered, partly bovine locus can comprise a fully recombined V(D)J exon.

In a specific aspect of the invention, the transgenic non-bovine mammal is a rodent, preferably a mouse, comprising an exogenously introduced, engineered, partly bovine immunoglobulin locus comprising codons for multiple bovine $V_H$, bovine $D_H$, and bovine $J_H$ gene segments with intervening sequences, including a pre-D region, based on the intervening (non-coding) sequences in the rodent. In a particularly preferred aspect, the transgenic non-bovine rodent further comprises partly bovine Igl loci comprising coding sequences of bovine Vκ or Vλ genes, and Jκ or Jλ genes, respectively, in conjunction with intervening (non-coding) sequences corresponding to the immunoglobulin intervening sequences present in the Igl loci of the rodent.

In an exemplary embodiment, as set forth in more detail in the Examples section, the entire endogenous $V_H$ immunoglobulin locus of the mouse genome is deleted and subsequently replaced by 20 bovine $V_H$ gene segments containing interspersed non-coding sequences corresponding to the non-coding sequences of the J558 $V_H$ locus of the mouse genome. The complete, exogenously introduced, engineered immunoglobulin locus further comprises bovine $D_H$ and $J_H$ gene segments, as well as the 13 kb mouse pre-D region. Thus, the bovine $V_H$, $D_H$, and $J_H$ codon sequences are embedded in the mouse intergenic and intronic sequences.

The methods of the invention utilize a combination of homologous recombination and site-specific recombination to create the cells and animals of the invention. A homology targeting vector is first used to introduce the sequence-specific recombination sites into the mammalian host cell genome at the desired location in the endogenous immunoglobulin loci. Preferably, in the absence of a recombinase protein, the sequence-specific recombination site inserted into the genome of a mammalian host cell by homologous recombination does not affect expression and amino acid codons of any genes in the mammalian host cell. This approach maintains the proper transcription and translation of the immunoglobulin genes which produce the desired antibody after insertion of recombination sites and, optionally, any additional sequence such as a selectable marker gene. However, in some cases it is possible to insert a recombinase site and other sequences into an immunoglobulin locus sequence such that an amino acid sequence of the antibody molecule is altered by the insertion, but the antibody still retains sufficient functionality for the desired purpose. Examples of such codon-altering homologous recombination may include the introduction of polymorphisms into the endogenous locus and changing the constant region exons so that a different isotype is expressed from the endogenous locus. The invention envisions encompassing such insertions as well.

In specific aspects of the invention, the homology targeting vector can be utilized to replace certain sequences within the endogenous genome as well as to insert certain sequence-specific recombination sites and one or more selectable marker genes into the host cell genome. It is understood by those of ordinary skill in the art that a selectable marker gene as used herein can be exploited to weed out individual cells that have not undergone homologous recombination and cells that harbor random integration of the targeting vector.

Exemplary methodologies for homologous recombination are described in U.S. Pat. Nos. 6,689,610; 6,204,061; 5,631,153; 5,627,059; 5,487,992; and 5,464,764, each of which is incorporated by reference in its entirety.

Site/Sequence-Specific Recombination

Site/sequence-specific recombination differs from general homologous recombination in that short specific DNA sequences, which are required for the recombinase recognition, are the only sites at which recombination occurs. Depending on the orientations of these sites on a particular DNA strand or chromosome, the specialized recombinases that recognize these specific sequences can catalyze i) DNA excision or ii) DNA inversion or rotation. Site-specific recombination can also occur between two DNA strands if these sites are not present on the same chromosome. A number of bacteriophage- and yeast-derived site-specific recombination systems, each comprising a recombinase and specific cognate sites, have been shown to work in eukaryotic cells and are therefore applicable for use in the present invention, and these include the bacteriophage P1 Cre/lox, yeast FLP-FRT system, and the Dre system of the tyrosine family of site-specific recombinases. Such systems and methods of use are described, e.g., in U.S. Pat. Nos. 7,422,889; 7,112,715; 6,956,146; 6,774,279; 5,677,177; 5,885,836; 5,654,182; and 4,959,317, each of which is incorporated herein by reference to teach methods of using such recombinases.

Other systems of the tyrosine family of site-specific recombinases such as bacteriophage lambda integrase, HK2022 integrase, and in addition systems belonging to the separate serine family of recombinases such as bacteriophage phiC31, R4Tp901 integrases are known to work in mammalian cells using their respective recombination sites, and are also applicable for use in the present invention.

Since site-specific recombination can occur between two different DNA strands, site-specific recombination occurrence can be utilized as a mechanism to introduce an exogenous locus into a host cell genome by a process called recombinase-mediated cassette exchange (RMCE). The RMCE process can be exploited by the combined usage of wild-type and mutant sequence-specific recombination sites for the same recombinase protein together with negative selection. For example, a chromosomal locus to be targeted may be flanked by a wild-type LoxP site on one end and by a mutant LoxP site on the other. Likewise, an exogenous vector containing a sequence to be inserted into the host cell genome may be similarly flanked by a wild-type LoxP site on one end and by a mutant LoxP site on the other. When this exogenous vector is transfected into the host cell in the presence of Cre recombinase, Cre recombinase will catalyze RMCE between the two DNA strands, rather than the excision reactions on the same DNA strands, because the wild-type LoxP and mutant LoxP sites on each DNA strand are incompatible for recombination with each other. Thus, the LoxP site on one DNA strand will recombine with a LoxP site on the other DNA strand; similarly, the mutated LoxP site on one DNA strand will only recombine with a likewise mutated LoxP site on the other DNA strand.

The methods of the invention preferably utilize combined variants of the sequence-specific recombination sites that are recognized by the same recombinase for RMCE. Examples of such sequence-specific recombination site variants include those that contain a combination of inverted repeats or those which comprise recombination sites having mutant spacer sequences. For example, two classes of variant recombinase sites are available to engineer stable Cre-loxP integrative recombination. Both exploit sequence mutations in the Cre recognition sequence, either within the 8 bp spacer region or the 13-bp inverted repeats. Spacer mutants such as lox511 (Hoess, et al., Nucleic Acids Res, 14:2287-2300 (1986)), lox5171 and lox2272 (Lee and Saito, Gene, 216:55-65 (1998)), m2, m3, m7, and m11 (Langer, et al., Nucleic Acids Res, 30:3067-3077 (2002)) recombine readily with themselves but have a markedly reduced rate of recombination with the wild-type site. This class of mutants has been exploited for DNA insertion by RMCE using non-interacting Cre-Lox recombination sites and non-interacting FLP recombination sites (Baer and Bode, Curr Opin Biotechnol, 12:473-480 (2001); Albert, et al., Plant J, 7:649-659 (1995); Seibler and Bode, Biochemistry, 36:1740-1747 (1997); Schlake and Bode, Biochemistry, 33:12746-12751 (1994)).

Inverted repeat mutants represent the second class of variant recombinase sites. For example, LoxP sites can contain altered bases in the left inverted repeat (LE mutant) or the right inverted repeat (RE mutant). An LE mutant, lox71, has 5 bp on the 5' end of the left inverted repeat that is changed from the wild type sequence to TACCG (Araki, et al, Nucleic Acids Res, 25:868-872 (1997)). Similarly, the RE mutant, lox66, has the five 3'-most bases changed to CGGTA. Inverted repeat mutants are used for integrating plasmid inserts into chromosomal DNA with the LE mutant designated as the "target" chromosomal loxP site into which the "donor" RE mutant recombines. Post-recombination, loxP sites are located in cis, flanking the inserted segment. The mechanism of recombination is such that post-recombination one loxP site is a double mutant (containing both the LE and RE inverted repeat mutations) and the other is wild type (Lee and Sadowski, Prog Nucleic Acid Res Mol Biol, 80:1-42 (2005); Lee and Sadowski, J Mol Biol, 326: 397-412 (2003)). The double mutant is sufficiently different from the wild-type site that it is unrecognized by Cre recombinase and the inserted segment is not excised.

In certain aspects, sequence-specific recombination sites can be introduced into introns, as opposed to coding nucleic acid regions or regulatory sequences. This avoids inadvertently disrupting any regulatory sequences or coding regions necessary for proper antibody expression upon insertion of sequence-specific recombination sites into the genome of the animal cell.

Introduction of the sequence-specific recombination sites may be achieved by conventional homologous recombination techniques. Such techniques are described in references such as e.g., Sambrook and Russell (2001) (Molecular cloning: a laboratory manual 3rd ed. (Cold Spring Harbor, N.Y.: Cold Spring Harbor Laboratory Press) and Nagy, A. (2003). (Manipulating the mouse embryo: a laboratory manual, 3rd ed. (Cold Spring Harbor, N.Y.: Cold Spring Harbor Laboratory Press). Genetic Recombination: Nucleic acid, Homology (biology), Homologous recombination, Non-homologous end joining, DNA repair, Bacteria, Eukaryote, Meiosis, Adaptive immune system, V(D)J recombination by Frederic P. Miller, Agnes F. Vandome, and John McBrewster (Paperback—Dec. 23, 2009).

Specific recombination into the genome can be facilitated using vectors designed for positive or negative selection as known in the art. In order to facilitate identification of cells that have undergone the replacement reaction, an appropriate genetic marker system may be employed and cells selected by, for example, use of a selection tissue culture medium. However, in order to ensure that the genome sequence is substantially free of extraneous nucleic acid sequences at or adjacent to the two end points of the replacement interval, desirably the marker system/gene can be removed following selection of the cells containing the replaced nucleic acid.

In one preferred aspect of the methods of the present invention, cells in which the replacement of all or part of the endogenous immunoglobulin locus has taken place are negatively selected against upon exposure to a toxin or drug. For example, cells that retain expression of HSV-TK can be selected against by using nucleoside analogues such as ganciclovir. In another aspect of the invention, cells comprising the deletion of the endogenous immunoglobulin locus may be positively selected for by use of a marker gene, which can optionally be removed from the cells following or as a result of the recombination event. A positive selection system that may be used is based on the use of two non-functional portions of a marker gene, such as HPRT, that are brought together through the recombination event. These two portions are brought into functional association upon a successful replacement reaction being carried out and wherein the functionally reconstituted marker gene is flanked on either side by further sequence-specific recombination sites (which are different from the sequence-specific recombination sites used for the replacement reaction), such that the marker gene can be excised from the genome, using an appropriate site-specific recombinase.

The recombinase may be provided as a purified protein, or as a protein expressed from a vector construct transiently transfected into the host cell or stably integrated into the host cell genome. Alternatively, the cell may be used first to generate a transgenic animal, which then may be crossed with an animal that expresses said recombinase.

Because the methods of the invention can take advantage of two or more sets of sequence-specific recombination sites within the engineered genome, multiple rounds of RMCE can be exploited to insert the partly bovine immunoglobulin variable region genes into a non-bovine mammalian host cell genome.

Although not yet routine for the insertion of large DNA segments, CRISPR technology is another method to introduce the chimeric bovine Ig locus.

Generation of Transgenic Animals

In specific aspects, the invention provides methods for the creation of transgenic animals, preferably rodents, and more preferably mice, comprising the introduced, partly bovine immunoglobulin locus.

In one aspect, the host cell utilized for replacement of the endogenous immunoglobulin genes is an embryonic stem (ES) cell, which can then be utilized to create a transgenic mammal. Thus, in accordance with one aspect, the methods of the invention further comprise: isolating an embryonic stem cell which comprises the introduced, partly bovine immunoglobulin locus and using said ES cell to generate a transgenic animal that contains the replaced partly bovine immunoglobulin locus.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to terms and numbers used (e.g., vectors, amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

The examples illustrate targeting by both a 5' vector and a 3' vector that flank a site of recombination and introduction of synthetic DNA. It will be apparent to one skilled in art upon reading the specification that the 5' vector targeting can take place first followed by the 3', or the 3' vector targeting can take place followed by the 5' vector. In some circumstances, targeting can be carried out simultaneously with dual detection mechanisms.

Figure 2:
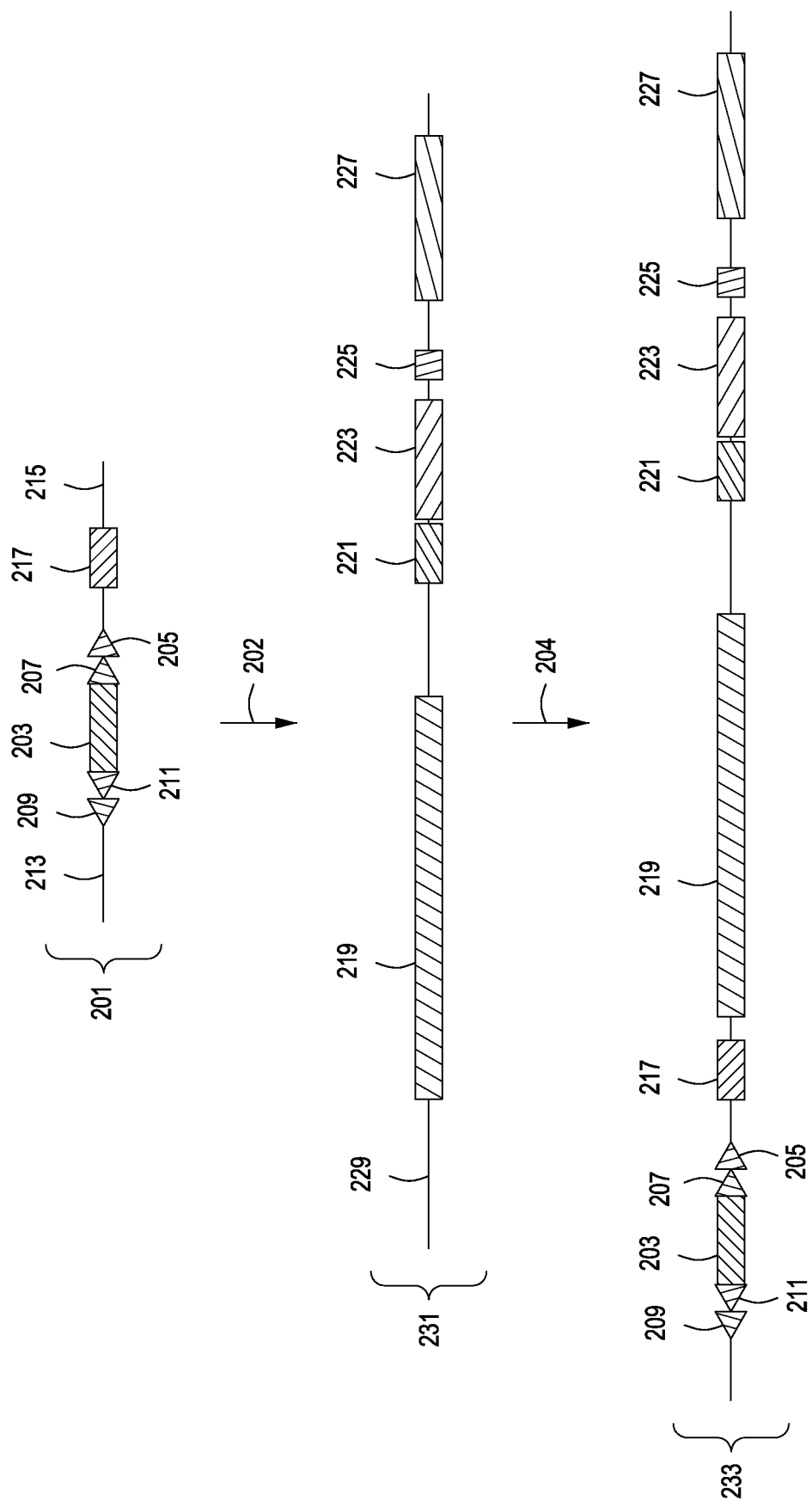
FIG. 2 is a schematic diagram illustrating the strategy of targeting by homologous recombination to introduce a first set of sequence-specific recombination sites into a region upstream of the H chain variable region gene locus in the genome of a non-bovine mammalian host cell.

Example 1: Introduction of an Engineered, Partly Bovine Immunoglobulin Variable Region Gene Locus into the Immunoglobulin H Chain Variable Region Gene Locus of a Non-Bovine Mammalian Host Cell Genome An exemplary method illustrating the introduction of an engineered, partly bovine immunoglobulin locus into the genomic locus of a non-mammalian ES cell is illustrated in more detail in FIGS. 2-6. In FIG. 2, a homology targeting vector (201) is provided comprising a puromycin phosphotransferase-thymidine kinase fusion protein (puro-TK) (203) flanked by two different recombinase recognition sites (e.g., FRT (207) and loxP (205) for Flp and Cre, respectively) and two different mutant sites (e.g., modified mutant FRT (209) and mutant loxP (211)) that lack the ability to recombine with their respective wild-type counterparts/sites (i.e., wild-type FRT (207) and wild-type loxP (205)). The targeting vector comprises a diphtheria toxin receptor (DTR) cDNA (217) for use in negative selection of cells containing the introduced construct in future steps. The targeting vector also optionally comprises a visual marker such as a green fluorescent protein (GFP) (not shown). The regions 213 and 215 are homologous to the 5' and 3' portions, respectively, of a contiguous region (229) in the endogenous non-bovine locus that is 5' of the genomic region comprising the endogenous, non-bovine $V_H$ gene segments (219). The homology targeting vector (201) is introduced (202) into the ES cell, which has an immunoglobulin locus (231) comprising endogenous $V_H$ gene segments (219), the pre-D region (221), $D_H$ (223) genes, $J_H$ gene segments (225), and the immunoglobulin constant region genes (227). The site-specific recombination sequences and the DTR cDNA from the homology targeting vector (201) are integrated (204) into the non-bovine genome at a site 5' of the endogenous mouse $V_H$ gene locus, resulting in the genomic structure illustrated at 233. The ES cells that do not have the exogenous vector (201) integrated into their genome can be selected against (killed) by including puromycin in the culture medium; only the ES cells that have stably integrated the exogenous vector (201) into their genome and constitutively express the puro-TK gene are resistant to puromycin.

Figure 3:
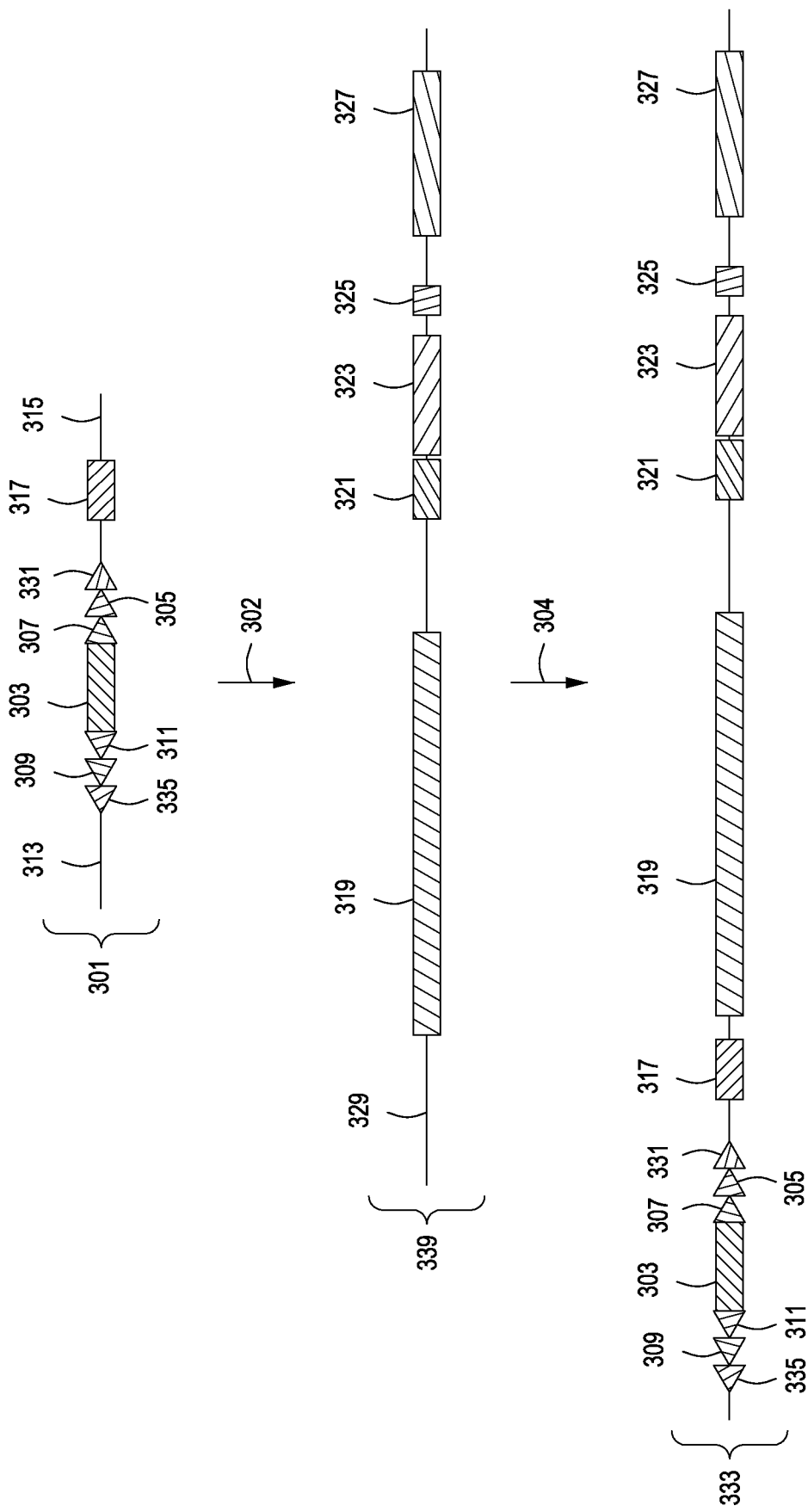
FIG. 3 is another schematic diagram illustrating the strategy of targeting by homologous recombination to introduce a first set of sequence-specific recombination sites into a region upstream of the H chain variable region gene locus in the genome of a non-bovine mammalian host cell.

FIG. 3 illustrates effectively the same approach as FIG. 2, except that an additional set of sequence-specific recombination sites is added, e.g., a Rox site (331) and a modified Rox site (335) for use with the Dre recombinase. In FIG. 3 a homology targeting vector (301) is provided comprising a puro-TK fusion protein (303) flanked by wild-type recombinase-recognition sites FRT (307), loxP (305), and Rox (331) and mutant sites for Flp (309), Cre (311), and Dre (335) recombinases that lack the ability to recombine with the wild-type sites 307, 305 and 331, respectively. The targeting vector also comprises a diphtheria toxin receptor (DTR) cDNA (317). The regions 313 and 315 are homologous to the 5' and 3' portions, respectively, of a contiguous region (329) in the endogenous non-bovine locus (339) that is 5' of the genomic region comprising the endogenous mouse $V_H$ gene segments (319). The homology targeting vector is introduced (302) into the mouse immunoglobulin locus (339), which comprises the endogenous $V_H$ gene segments (319), the pre-D region (321), the $D_H$ gene segments (323), the $J_H$ gene segments (325), and the constant region genes (327) of the Igh locus. The site-specific recombination sequences and the DTR cDNA (317) in the homology targeting vector (301) are integrated (304) into the mouse genome at a site 5' of the endogenous mouse $V_H$ gene locus (319), resulting in the genomic structure illustrated at 333.

Figure 4:
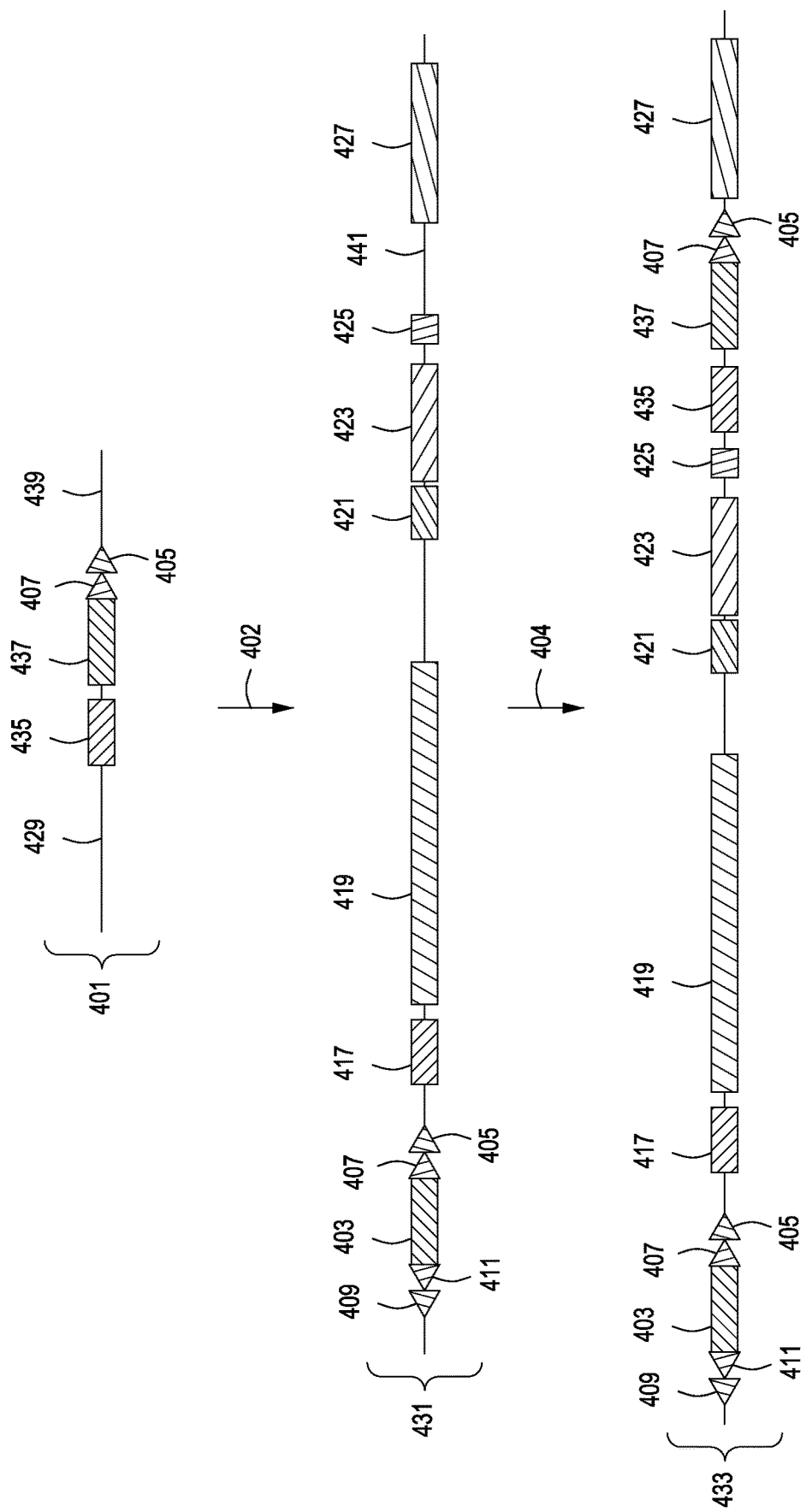
FIG. 4 is a schematic diagram illustrating the introduction of a second set of sequence-specific recombination sites into a region downstream of the H chain variable region gene locus in the genome of a non-bovine mammalian cell via a homology targeting vector.

As illustrated in FIG. 4, a second homology targeting vector (401) is provided comprising an optional hypoxanthine-guanine phosphoribosyltransferase (HPRT) gene (435) that can be used for positive selection in HPRT-deficient ES cells; a neomycin resistance gene (437); recombinase-recognition sites FRT (407) and loxP (405) for Flp and Cre, respectively, which have the ability to recombine with FRT (407) and loxP (405) sites previously integrated into the mouse genome from the first homology targeting vector. The previous homology targeting vector also consists of mutant FRT site (409), mutant loxP site (411), a puro-TK fusion protein cDNA (403), and a DTR cDNA at a site 5' of the endogenous mouse $V_H$ gene locus (419). The regions 429 and 439 are homologous to the 5' and 3' portions, respectively, of a contiguous region (441) in the endogenous non-bovine locus that is downstream of the endogenous $J_H$ gene segments (425) and upstream of the constant region genes (427). The homology targeting vector is introduced (402) into the modified mouse immunoglobulin locus (431), which comprises the endogenous $V_H$ gene segments (419), the pre-D region (421), the $D_H$ gene segments (423), the $J_H$ gene segments (425), and the constant region genes (427). The site-specific recombination sequences (407, 405), the HPRT gene (435) and a neomycin resistance gene (437) of the homology targeting vector are integrated (404) into the mouse genome upstream of the endogenous mouse constant region genes (427), resulting in the genomic structure illustrated at 433.

Figure 5:
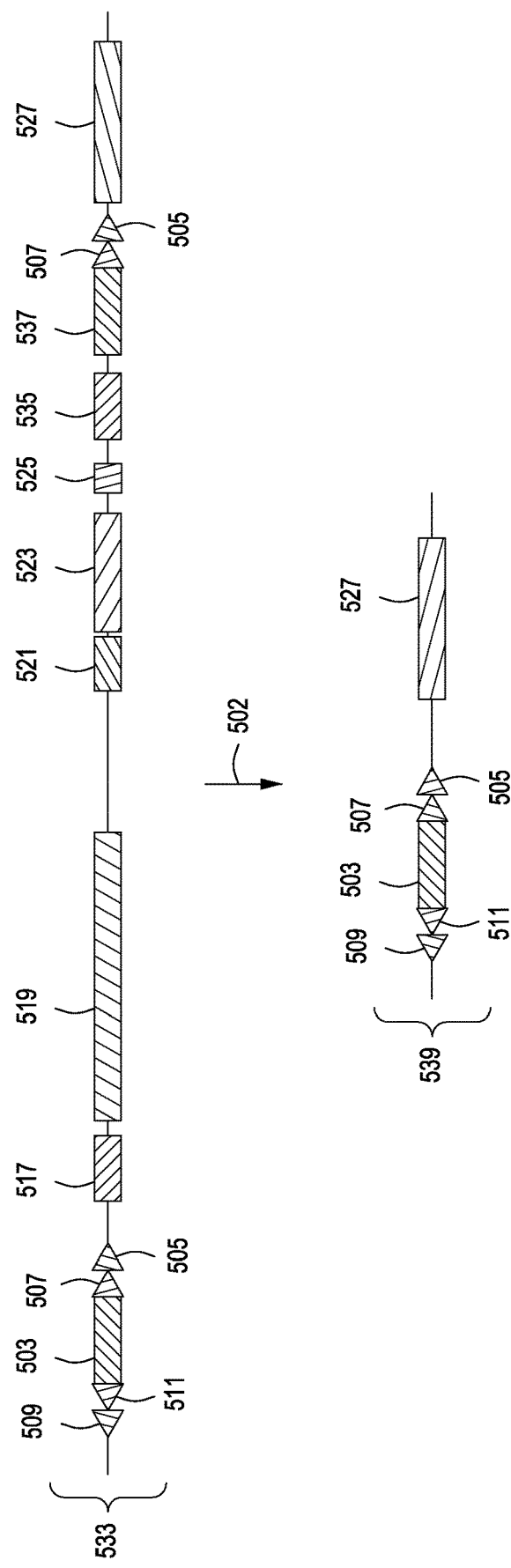
FIG. 5 is a schematic diagram illustrating deletion of the endogenous immunoglobulin H chain variable region genes from the genome of the non-bovine mammalian host cell.

Once the recombination sites are integrated into the mammalian host cell genome, the endogenous region of the immunoglobulin domain is then subjected to recombination by introducing one of the recombinases corresponding to the sequence-specific recombination sites integrated into the genome, e.g., either Flp or Cre. Illustrated in FIG. 5, is a modified Igh locus of the mammalian host cell genome comprising two integrated DNA fragments. One fragment comprising mutant FRT site (509), mutant LoxP site (511), puro-TK gene (503), wild-type FRT site (507), and wild-type LoxP site (505), and DTR cDNA (517) is integrated upstream of the $V_H$ gene locus (519). The other DNA fragment comprising HPRT gene (535), neomycin resistance gene (537), wild-type FRT site (507), and wild-type LoxP site (505) is integrated downstream of the pre-D (521), $D_H$ (523) and $J_H$ (525) gene loci, but upstream of the constant region genes (527). In the presence of Flp or Cre (502), all the intervening sequences between the wild-type FRT or wild-type LoxP sites—including the DTR gene (517), the endogenous Igh variable region gene loci (519, 521, 525), and the HPRT (535) and neomycin resistance (537) genes—are deleted, resulting in a genomic structure illustrated in 539. The procedure depends on the second targeting having occurred on the same chromosome rather than on its homolog (i.e., in cis rather than in trans). If the targeting occurs in cis as intended in this invention, the cells are not sensitive to negative selection after Cre- or Flp-mediated recombination by diphtheria toxin introduced into the media, because the DTR gene which causes sensitivity to diphtheria toxin should be absent (deleted) from the host cell genome. Likewise, ES cells that harbor random integration of the first and/or second targeting vector(s) are rendered sensitive to diphtheria toxin by presence of the undeleted DTR gene.

ES cells that are insensitive to diphtheria toxin are then screened for the deletion of the endogenous variable region gene loci. The primary screening method for the deleted endogenous immunoglobulin locus can be carried out by Southern blotting, or by polymerase chain reaction (PCR) followed by confirmation with a secondary screening technique such as Southern blotting.

Figure 6:
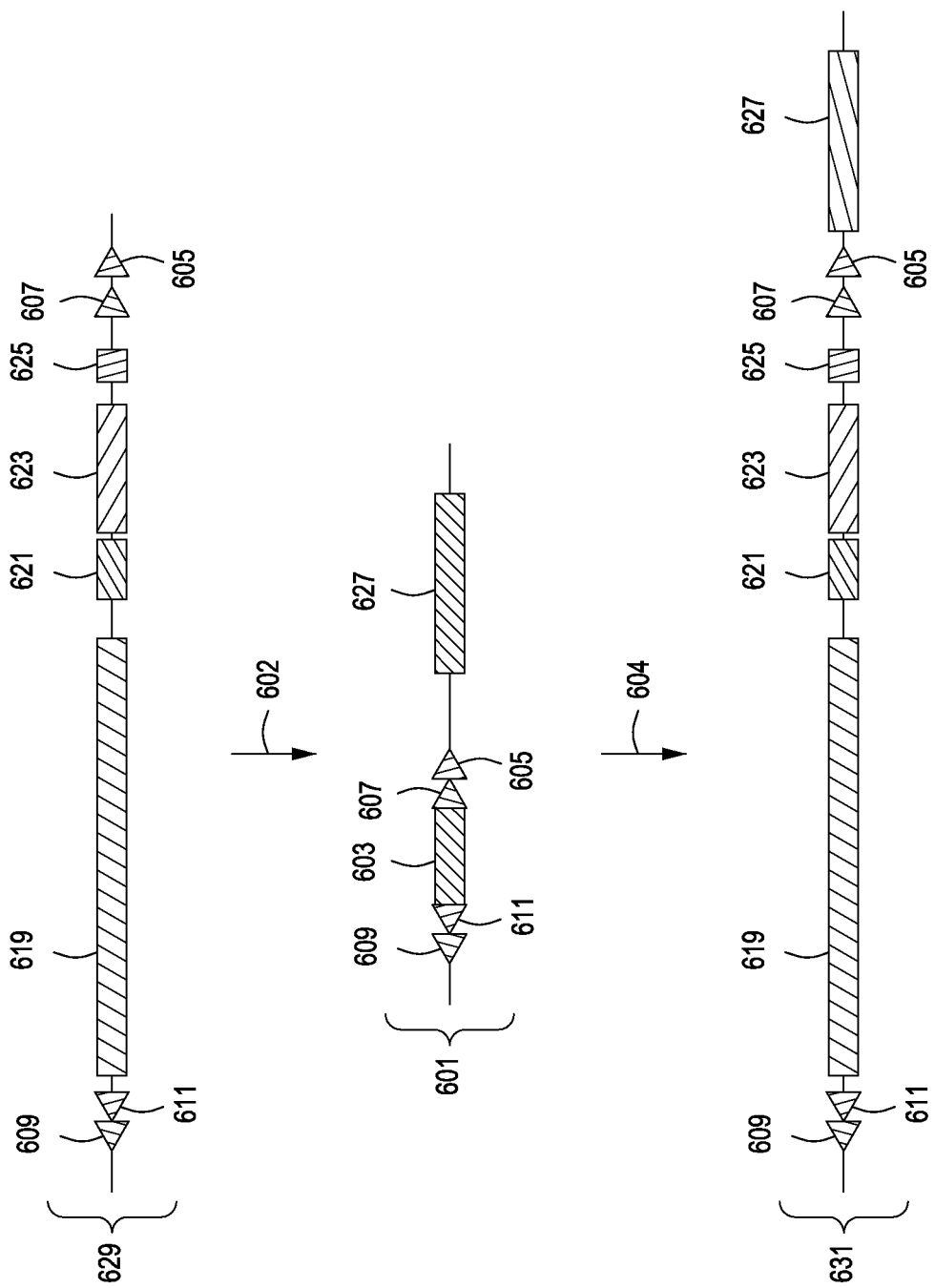
FIG. 6 is a schematic diagram illustrating the RMCE strategy to introduce an engineered, partly bovine immunoglobulin H chain locus into the non-bovine mammalian host cell genome that has been previously modified to delete the endogenous immunoglobulin H chain variable region genes.

FIG. 6 illustrates introduction of the engineered, partly bovine sequence into a non-bovine genome previously modified to delete part of the endogenous Igh locus that encodes the heavy chain variable region domains as well as all the intervening sequences between the $V_H$ and $J_H$ gene loci. A site-specific targeting vector (629) comprising partly bovine $V_H$ gene locus (619), endogenous non-bovine pre-D gene region (621), partly bovine $D_H$ gene locus (623), partly bovine $J_H$ gene locus (625), as well as flanking mutant FRT (609), mutant LoxP (611), wild-type FRT (607), and wild-type LoxP (605) sites is introduced (602) into the host cell. Specifically, the partly bovine $V_H$ locus (619) comprises 20 bovine $V_H$ coding sequences in conjunction with the intervening sequences based on the endogenous non-bovine genome sequences; the pre-D region (621) comprises a 21.6 kb endogenous non-bovine sequence with significant homology to the corresponding region of the bovine Igh locus; the $D_H$ gene locus (623) comprises codons of 10 $D_H$ gene segments embedded in the intervening sequences surrounding the endogenous non-bovine $D_H$ gene segments; and the $J_H$ gene locus (625) comprises codons of 4 bovine $J_H$ gene segments embedded in the intervening sequences based on the endogenous non-bovine genome. The Igh locus (601) of the host cell genome has been previously modified to delete all the $V_H$, $D_H$, and $J_H$ gene segments including the intervening sequences as described in FIG. 5. As a consequence of this modification, the endogenous non-bovine host cell Igh locus (601) is left with a puro-TK fusion gene, which is flanked by a mutant FRT site (609) and a mutant LoxP site (611) upstream as well as a wild-type FRT (607) and a wild-type LoxP (605) downstream. Upon introduction of the appropriate recombinase (604), the partly bovine immunoglobulin locus (629) is integrated into the genome upstream of the endogenous non-bovine constant region genes (627), resulting in the genomic structure illustrated at 631.

The sequences of the bovine $V_H$, $D_H$ and $J_H$ gene segment coding regions are in Table 1.

A primary screening procedure for the introduction of the partly bovine immunoglobulin locus can be carried out by Southern blotting, or by PCR with confirmations from secondary screening methods such as Southern blotting. The screening methods are designed to detect the presence of the inserted $V_H$ and/or $J_H$ gene loci, as well as all the intervening sequences.

Figure 7:
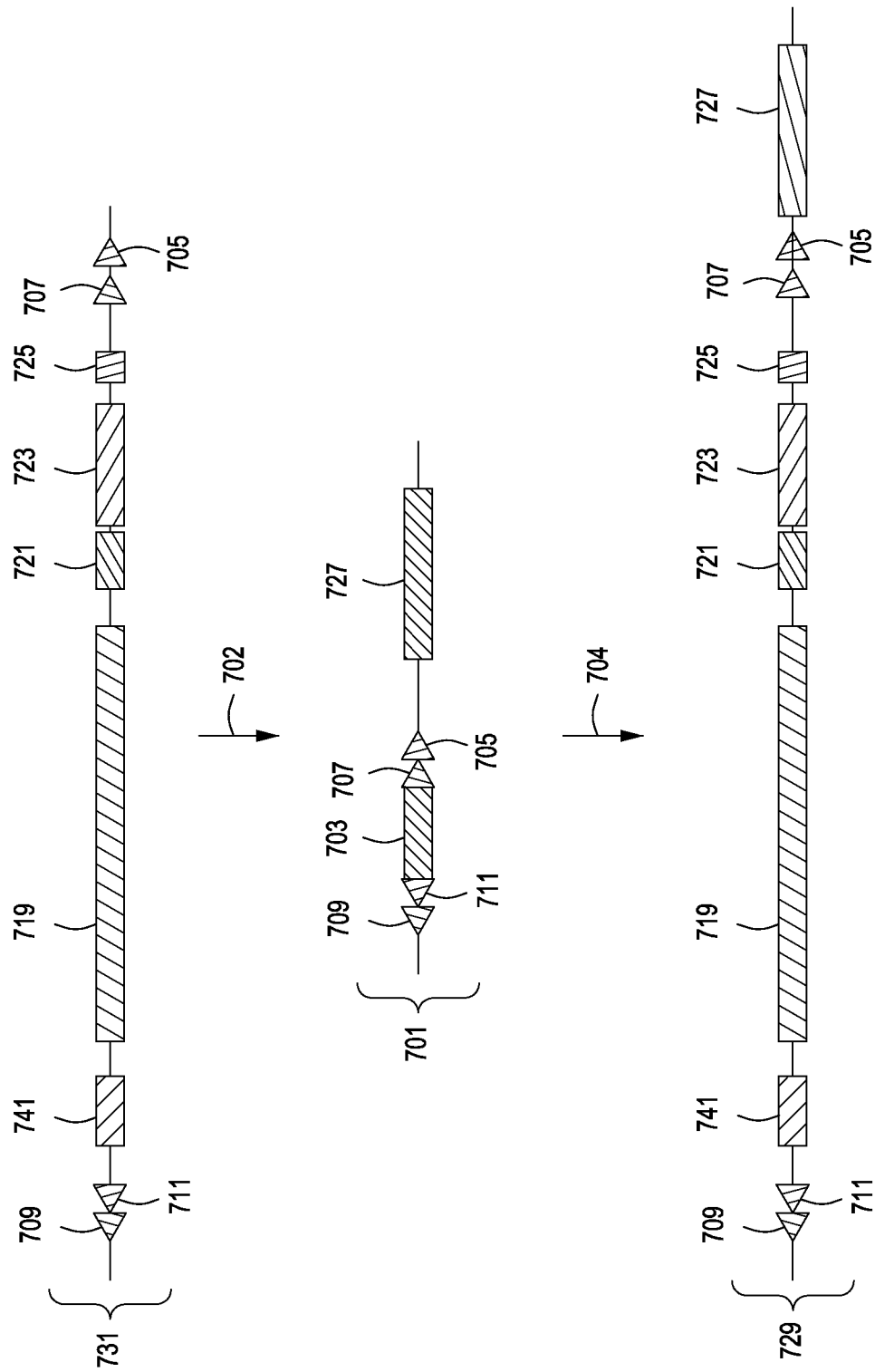
FIG. 7 is a schematic diagram illustrating the RMCE strategy to introduce an engineered, partly bovine immunoglobulin H chain locus comprising additional regulatory sequences into the non-bovine mammalian host cell genome that has been previously modified to delete the endogenous immunoglobulin H chain variable region genes.

Example 2: Introduction of an Engineered, Partly Bovine Immunoglobulin Variable Region Gene Locus Comprising Additional Non-Coding Regulatory or Scaffold Sequences into the Immunoglobulin H Chain Variable Region Gene Locus of a Non-Bovine Mammalian Host Cell Genome In certain aspects, the partly bovine immunoglobulin locus comprises the elements as described in Example 1, but with additional non-coding regulatory or scaffold sequences e.g., sequences strategically added to introduce additional regulatory sequences, to ensure the desired spacing within the introduced immunoglobulin locus, to ensure that certain coding sequences are in adequate juxtaposition with other sequences adjacent to the replaced immunoglobulin locus, and the like. FIG. 7 illustrates the introduction of a second exemplary engineered, partly bovine sequence to the modified non-bovine genome as produced in FIGS. 2-5 and described in Example 1 above.

FIG. 7 illustrates introduction of the engineered, partly bovine sequence into the mouse genome previously modified to delete part of the endogenous non-bovine Igh locus that encodes the heavy chain variable region domains as well as all the intervening sequences between the endogenous $V_H$ and $J_H$ gene loci. A site-specific targeting vector (731) comprising an engineered, partly bovine immunoglobulin locus to be inserted into the non-bovine host genome is introduced (702) into the genomic region (701). The site-specific targeting vector (731) comprising a partly bovine $V_H$ gene locus (719), mouse pre-D region (721), partly bovine $D_H$ gene locus (723), partly bovine $J_H$ gene locus (725), PAIR elements (741, described above at [00069]), as well as flanking mutant FRT (709), mutant LoxP (711) wild-type FRT (707) and wild-type LoxP (705) sites is introduced (702) into the host cell. Specifically, the engineered, partly bovine $V_H$ gene locus (719) comprises 20 bovine $V_H$ gene segment coding regions in conjunction with intervening sequences based on the endogenous non-bovine genome sequences; the pre-D region (721) comprises a 21.6 kb non-bovine sequence present upstream of the endogenous non-bovine genome; the $D_H$ region (723) comprises codons of 10 bovine $D_H$ gene segments embedded in the intervening sequences surrounding the endogenous non-bovine $D_H$ gene segments; and the $J_H$ gene locus (725) comprises codons of 4 bovine $J_H$ gene segments embedded in the intervening sequences based on the endogenous non-bovine genome sequences. The Igh locus (701) of the host cell genome has been previously modified to delete all the $V_H$, $D_H$, and $J_H$ gene segments including the intervening sequences as described in relation to FIG. 5. As a consequence of this modification, the endogenous non-bovine Igh locus (701) is left with a puro-TK fusion gene (703), which is flanked by a mutant FRT site (709) and a mutant LoxP site (711) upstream as well as a wild-type FRT (707) and a wild-type LoxP (705) downstream. Upon introduction of the appropriate recombinase (704), the partly bovine immunoglobulin locus is integrated into the genome upstream of the endogenous mouse constant region genes (727), resulting in the genomic structure illustrated at 729.

The primary screening procedure for the introduction of the engineered, partly bovine immunoglobulin locus can be carried out by Southern blotting or by PCR with confirmations from secondary screening methods such as Southern blotting. The screening methods are designed to detect the presence of the inserted $V_H$ and/or $J_H$ gene loci, as well as all the intervening sequences.

Figure 8:
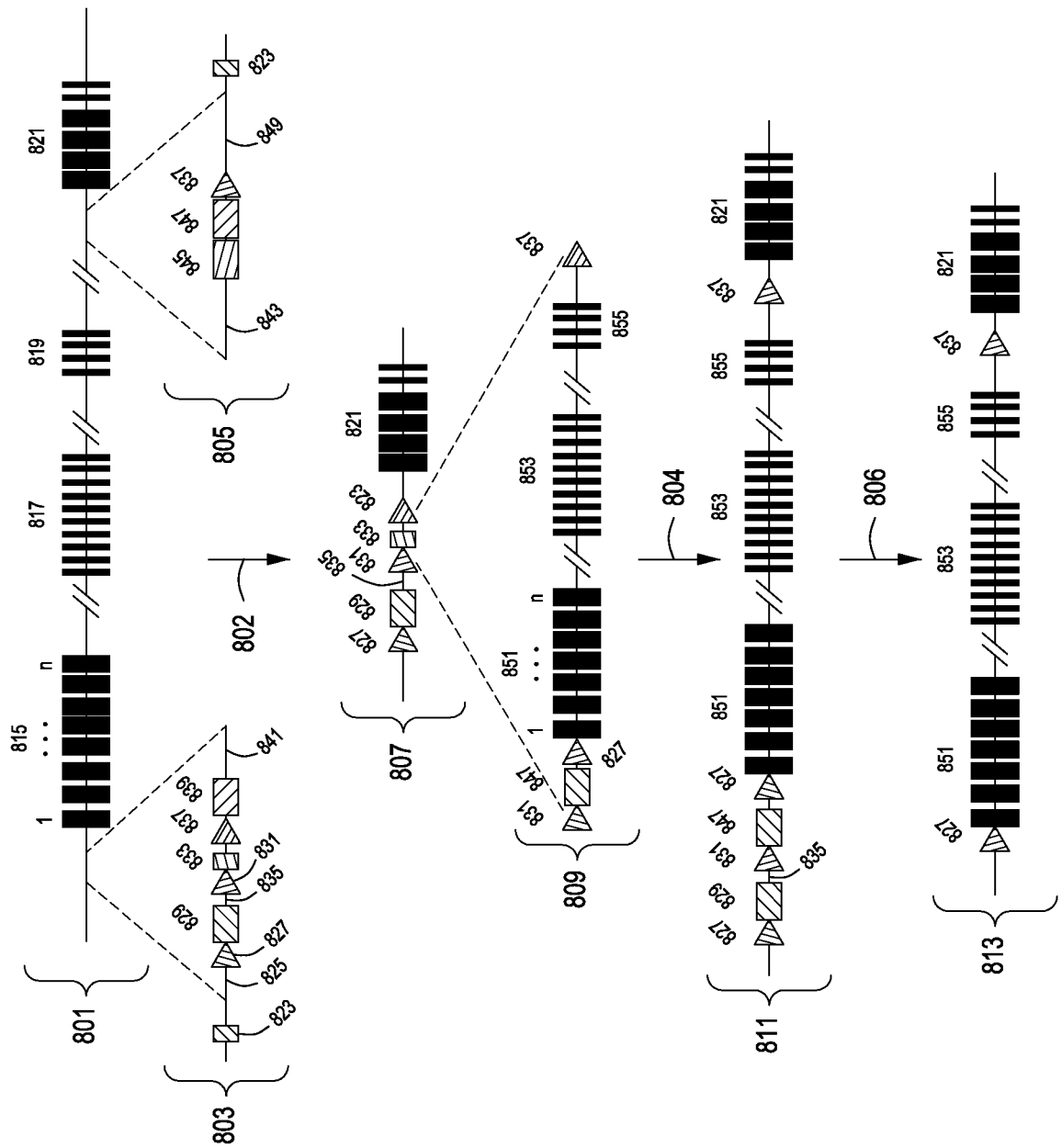
FIG. 8 is a schematic diagram illustrating the introduction of an engineered, partly bovine immunoglobulin H chain variable region gene locus into the endogenous immunoglobulin H chain locus of the mouse genome.

Example 3: Introduction of an Engineered, Partly Bovine Immunoglobulin Locus into the Immunoglobulin Heavy Chain Gene Locus of a Mouse Genome A method for replacing a portion of a mouse genome with an engineered, partly bovine immunoglobulin locus is illustrated in FIG. 8. This method uses introduction of a first site-specific recombinase recognition sequence into the mouse genome followed by the introduction of a second site-specific recombinase recombination sequence into the mouse genome. The two sites flank the entire clusters of endogenous mouse $V_H$, $D_H$ and $J_H$ region gene segments. The flanked region is deleted using the relevant site-specific recombinase, as described herein.

The targeting vectors (803, 805) employed for introducing the site-specific recombinase sites on either side of the $V_H$ (815), $D_H$ (817) and $J_H$ (819) region gene segment cluster and upstream of the constant region genes (821) in the wild-type mouse immunoglobulin locus (801) include an additional site-specific recombination sequence that has been modified so that it is still recognized efficiently by the recombinase, but does not recombine with unmodified sites. This mutant modified site (e.g., lox5171) is positioned in the targeting vector such that after deletion of the endogenous $V_H$, $D_H$, and $J_H$ gene segments (802) it can be used for a second site-specific recombination event in which a non-native piece of DNA is moved into the modified Igh locus by RMCE. In this example, the non-native DNA is a synthetic nucleic acid comprising both bovine and non-bovine sequences (809).

Two gene targeting vectors are constructed to accomplish the process just outlined. One of the vectors (803) comprises a mouse genomic DNA taken from the 5' end of the Igh locus, upstream of the most distal $V_H$ gene segment. The other vector (805) comprises mouse genomic DNA taken from within the locus downstream of the $J_H$ gene segments.

The key features of the 5' vector (803) in order from 5' to 3' are as follows: a gene encoding the diphtheria toxin A (DTA) subunit under transcriptional control of a modified herpes simplex virus type I thymidine kinase gene promoter coupled to two mutant transcriptional enhancers from the polyoma virus (823); 4.5 Kb of mouse genomic DNA mapping upstream of the most distal $V_H$ gene segment in the Igh locus (825); a FRT recognition sequence for the Flp recombinase (827); a piece of genomic DNA containing the mouse Polr2a gene promoter (829); a translation initiation sequence (methionine codon embedded in a "Kozak" consensus sequence, 835); a mutated loxP recognition sequence (lox5171) for the Cre recombinase (831); a transcription termination/polyadenylation sequence (pA, 833); a loxP recognition sequence for the Cre recombinase (837); a gene encoding a fusion protein comprised of a protein conferring resistance to puromycin fused to a truncated form of the thymidine kinase (pu-TK) under transcriptional control of the promoter from the mouse phosphoglycerate kinase 1 gene (839); and 3 Kb of mouse genomic DNA (841) mapping close to the 4.5 Kb mouse genomic DNA sequence present near the 5' end of the vector and arranged in the native relative orientation.

The key features of the 3' vector (805) in order from 5' to 3' are as follows: 3.7 Kb of mouse genomic DNA mapping within the intron between the $J_H$ and $C_H$ gene loci (843); an HPRT gene under transcriptional control of the mouse Polr2a gene promoter (845); a neomycin resistance gene under the control of the mouse phosphoglycerate kinase 1 gene promoter (847); a loxP recognition sequence for the Cre recombinase (837); 2.1 Kb of mouse genomic DNA (849) that maps immediately downstream in the 3.7 Kb mouse genomic DNA fragment present near the 5' end of the vector and arranged in the native relative orientation; and a gene encoding the DTA subunit under transcriptional control of a modified herpes simplex virus type I thymidine kinase gene promoter coupled to two mutant transcriptional enhancers from the polyoma virus (823).

Mouse embryonic stem (ES) cells (derived from C57B1/6NTac mice) are transfected by electroporation with the 3' vector (805) according to widely used procedures. Prior to electroporation, the vector DNA is linearized with a rare-cutting restriction enzyme that cuts only in the prokaryotic plasmid sequence or the polylinker associated with it. The transfected cells are plated and after ~24 hours they are placed under positive selection for cells that have integrated the 3' vector into their DNA by using the neomycin analogue drug G418. There is also negative selection for cells that have integrated the vector into their DNA but not by homologous recombination. Non-homologous recombination will result in retention of the DTA (823) gene, which will kill the cells when the gene is expressed, whereas the DTA gene is deleted by homologous recombination since it lies outside of the region of vector homology with the mouse Igh locus. Colonies of drug-resistant ES cells are physically extracted from their plates after they became visible to the naked eye about a week later. These picked colonies are disaggregated, re-plated in micro-well plates, and cultured for several days. Thereafter, each of the clones of cells is divided such that some of the cells can be frozen as an archive, and the rest used for isolation of DNA for analytical purposes.

DNA from the ES cell clones is screened by PCR using a widely practiced gene-targeting assay design. For this assay one of the PCR oligonucleotide primer sequences maps outside the region of identity shared between the 3' vector (805) and the genomic DNA, while the other maps within the novel DNA between the two arms of genomic identity in the vector, i.e., in the HPRT (845) or neo (847) genes. According to the standard design, these assays detect pieces of DNA that would only be present in clones of ES cells derived from transfected cells that undergo fully legitimate homologous recombination between the 3' targeting vector and the endogenous mouse Igh locus. Two separate transfections are performed with the 3' vector (805). PCR-positive clones from the two transfections are selected for expansion followed by further analysis using Southern blot assays.

The Southern blot assays are performed according to widely used procedures using three probes and genomic DNA digested with multiple restriction enzymes chosen so that the combination of probes and digests allow the structure of the targeted locus in the clones to be identified as properly modified by homologous recombination. One of the probes maps to DNA sequence flanking the 5' side of the region of identity shared between the 3' targeting vector and the genomic DNA; a second probe maps outside the region of identity but on the 3' side; and the third probe maps within the novel DNA between the two arms of genomic identity in the vector, i.e., in the HPRT (845) or neo (847) genes. The Southern blot identifies the presence of the expected restriction enzyme-generated fragment of DNA corresponding to the correctly mutated, i.e., by homologous recombination with the 3' Igh targeting vector, part of the Igh locus as detected by one of the external probes and by the neomycin or HPRT probe. The external probe detects the mutant fragment and also a wild-type fragment from the non-mutant copy of the immunoglobulin Igh locus on the homologous chromosome.

Karyotypes of PCR and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. ES cell clones that are judged to have the expected correct genomic structure based on the Southern blot data—and that also do not have detectable chromosomal aberrations based on the karyotype analysis—are selected for further use.

Acceptable clones are then modified with the 5' vector (803) using procedures and screening assays that are essentially identical in design to those used with the 3' vector (805) except that puromycin selection is used instead of G418/neomycin selection. The PCR assays, probes and digests are also tailored to match the genomic region being modified by the 5' vector (805).

Clones of ES cells that have been mutated in the expected fashion by both the 3' and the 5' vectors—i.e., doubly targeted cells carrying both engineered mutations—are isolated following vector targeting and analysis. The clones must have undergone gene targeting on the same chromosome, as opposed to homologous chromosomes, i.e., the engineered mutations created by the targeting vectors must be in cis on the same DNA strand rather than in trans on separate homologous DNA strands. Clones with the cis arrangement are distinguished from those with the trans arrangement by analytical procedures such as fluorescence in situ hybridization of metaphase spreads using probes that hybridize to the novel DNA present in the two gene targeting vectors (803 and 805) between their arms of genomic identity. The two types of clones can also be distinguished from one another by transfecting them with a vector expressing the Cre recombinase, which deletes the pu-TK (839), HPRT (845) and neo (847) genes if the targeting vectors have been integrated in cis, and then comparing the number of colonies that survive gancyclovir selection against the thymidine kinase gene introduced by the 5' vector (803) and by analyzing the drug resistance phenotype of the surviving clones by a "sibling selection" screening procedure in which some of the cells from the clone are tested for resistance to puromycin or G418/neomycin. Cells with the cis arrangement of mutations are expected to yield approximately $10^3$ more ganciclovir-resistant clones than cells with the trans arrangement. The majority of the resulting cis-derived ganciclovir-resistant clones are also sensitive to both puromycin and G418/neomycin, in contrast to the trans-derived ganciclovir-resistant clones, which should retain resistance to both drugs. Doubly targeted clones of cells with the cis-arrangement of engineered mutations in the heavy chain locus are selected for further use.

The doubly targeted clones of cells are transiently transfected with a vector expressing the Cre recombinase and the transfected cells subsequently are placed under ganciclovir selection, as in the analytical experiment summarized above. Ganciclovir-resistant clones of cells are isolated and analyzed by PCR and Southern blot for the presence of the expected deletion between the two engineered mutations created by the 5' (803) and the 3' (805) targeting vectors. In these clones, the Cre recombinase causes a recombination (802) to occur between the loxP sites (837) introduced into the heavy chain locus by the two vectors to create the genomic DNA configuration shown at 807. Because the loxP sites are arranged in the same relative orientations in the two vectors, recombination results in excision of a circle of DNA comprising the entire genomic interval between the two loxP sites. The circle does not contain an origin of replication and thus is not replicated during mitosis and therefore is lost from the cells as they undergo expansion. The resulting clones carry a deletion of the DNA that was originally between the two loxP sites. Clones that have the expected deletion are selected for further use.

ES cell clones carrying the deletion of sequence in one of the two homologous copies of their immunoglobulin heavy chain locus are retransfected (804) with a Cre recombinase expression vector together with a piece of DNA (809) comprising a partly bovine immunoglobulin heavy chain locus containing part bovine/part mouse $V_H$, $D_H$ and $J_H$ region gene segments. The key features of this piece of synthetic DNA are the following: a lox5171 site (831); a neomycin resistance gene open reading frame (847) lacking the initiator methionine codon, but in-frame and contiguous with an uninterrupted open reading frame in the lox5171 site; a FRT site (827); an array of 20 bovine heavy chain variable region genes (851) each comprised of bovine coding sequences embedded in mouse noncoding sequences; optionally a 10 kb pre-D region from the mouse heavy chain locus (not shown); a 58 Kb piece of DNA containing the 10 bovine $D_H$ gene segments (853) and 4 bovine $J_H$ gene segments (855) each comprised of bovine coding sequences embedded in mouse noncoding sequences; a loxP site (837) in opposite relative orientation to the lox5171 site (831).

The transfected clones are placed under G418 selection, which enriches for clones of cells that have undergone RMCE in which the partly bovine donor DNA (809) is integrated in its entirety into the deleted immunoglobulin heavy chain locus between the lox5171 (831) and loxP sites (837) to create the DNA region illustrated at 811. Only cells that have properly undergone RMCE have the capability to express the neomycin resistance gene (847) because the promoter (829) as well as the initiator methionine codon (835) required for its expression are not present in the vector (809) and are already pre-existing in the host cell Igh locus (807). The remaining elements from the 5' vector (803) are removed via Flp-mediated recombination (806) in vitro or in vivo (as described in [000120]), resulting in the final bovine-based locus as shown at 813.

G418-resistant ES cell clones are analyzed by PCR and Southern blot to determine if they have undergone the expected RMCE process without unwanted rearrangements or deletions. Clones that have the expected genomic structure are selected for further use.

ES cell clones carrying the partly bovine immunoglobulin heavy chain DNA (813) in the mouse heavy chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here are of C57Bl/6NTac strain, and also carry a transgene encoding the Flp recombinase that is expressed in their germline. Offspring from these matings are analyzed for the presence of the partly bovine immunoglobulin heavy chain locus, and for loss of the FRT-flanked neomycin resistance gene that was created in the RMCE step. Mice that carry the partly bovine locus are used to establish a colony of mice.

Figure 9:
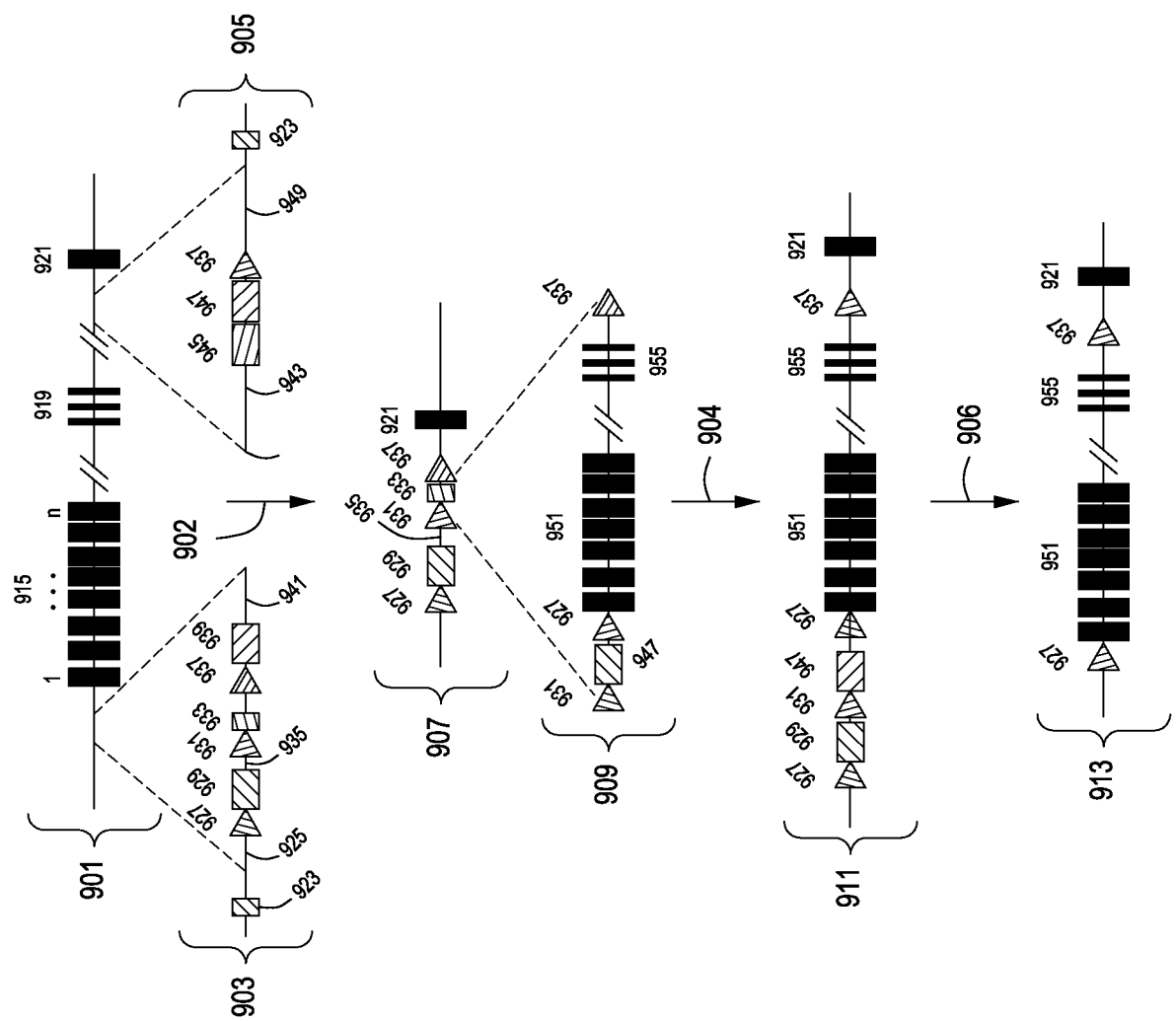
FIG. 9 is a schematic diagram illustrating the introduction of an engineered, partly bovine immunoglobulin κ L chain variable region gene locus into the endogenous immunoglobulin κ L chain locus of the mouse genome.

Example 4: Introduction of an Engineered, Partly Bovine Immunoglobulin Locus into the Immunoglobulin Kappa Chain Gene Locus of a Mouse Genome Another method for replacing a portion of a mouse genome with a partly bovine immunoglobulin locus is illustrated in FIG. 9. This method provides introducing a first site-specific recombinase recognition sequence into the mouse genome, which may be introduced either 5' or 3' of the cluster of endogenous $V_K$ (915) and $J_K$ (919) region genes of the mouse genome, followed by the introduction of a second site-specific recombinase recognition sequence into the mouse genome, which in combination with the first sequence-specific recombination site flanks the entire locus comprising clusters of $V_K$ and $J_K$ region gene segments upstream of the constant region genes (921). The flanked region is deleted and then replaced with a partly bovine immunoglobulin locus using the relevant site-specific recombinase, as described herein.

The targeting vectors employed for introducing the site-specific recombination sequences on either side of the $V_K$ (915) and $J_K$ (919) gene segments also include an additional site-specific recombination sequences that has been modified so that it is still recognized efficiently by the recombinase, but does not recombine with unmodified sites. This site is positioned in the targeting vector such that after deletion of the $V_K$ and $J_K$ gene segment clusters it can be used for a second site specific recombination event in which a non-native piece of DNA is moved into the modified $V_K$ locus via RMCE. In this example, the non-native DNA is a synthetic nucleic acid comprising both bovine and mouse Igκ variable region gene sequences.

Two gene targeting vectors are constructed to accomplish the process just outlined. One of the vectors (903) comprises mouse genomic DNA taken from the 5' end of the locus, upstream of the most distal $V_K$ gene segment. The other vector (905) comprises mouse genomic DNA taken from within the locus downstream (3') of the $J_K$ gene segments (919) and upstream of the constant region gene (921).

The key features of the 5' vector (903) are as follows: a gene encoding the diphtheria toxin A (DTA) subunit under transcriptional control of a modified herpes simplex virus type I thymidine kinase gene promoter coupled to two mutant transcriptional enhancers from the polyoma virus (923); 6 Kb of mouse genomic DNA (925) mapping upstream of the most distal variable region gene in the kappa chain locus; a FRT recognition sequence for the Flp recombinase (927); a piece of genomic DNA containing the mouse Polr2a gene promoter (929); a translation initiation sequence (935) methionine codon embedded in a "Kozak" consensus sequence); a mutated loxP recognition sequence (lox5171) for the Cre recombinase (931); a transcription termination/polyadenylation sequence (933); a loxP recognition sequence for the Cre recombinase (937); a gene encoding a fusion protein comprised of a protein conferring resistance to puromycin fused to a truncated form of the thymidine kinase (pu-TK) under transcriptional control of the promoter from the mouse phosphoglycerate kinase 1 gene (939); 2.5 Kb of mouse genomic DNA (941) mapping close to the 6 Kb sequence at the 5' end in the vector and arranged in the native relative orientation.

The key features of the 3' vector (905) are as follows: 6 Kb of mouse genomic DNA (943) mapping within the intron between the Jκ (919) and (921) CK gene loci; a gene encoding the human hypoxanthine-guanine phosphoribosyl transferase (HPRT) under transcriptional control of the mouse Polr2a gene promoter (945); a neomycin resistance gene under the control of the mouse phosphoglycerate kinase 1 gene promoter (947); a loxP recognition sequence for the Cre recombinase (937); 3.6 Kb of mouse genomic DNA (949) that maps immediately downstream in the genome of the 6 Kb fragment included at the 5' end in the vector, with the two fragments oriented in the same relative way as in the mouse genome; a gene encoding the diphtheria toxin A (DTA) subunit under transcriptional control of a modified herpes simplex virus type I thymidine kinase gene promoter coupled to two mutant transcriptional enhancers from the polyoma virus (923).

Mouse embryonic stem (ES) cells derived from C57B1/6NTac mice are transfected by electroporation with the 3' vector (905) according to widely used procedures. Prior to electroporation, the vector DNA is linearized with a rare-cutting restriction enzyme that cuts only in the prokaryotic plasmid sequence or the polylinker associated with it. The transfected cells are plated and after ~24 hours they are placed under positive selection for cells that have integrated the 3' vector into their DNA by using the neomycin analogue drug G418. There is also negative selection for cells that have integrated the vector into their DNA but not by homologous recombination. Non-homologous recombination will result in retention of the DTA gene, which will kill the cells when the gene is expressed, whereas the DTA gene is deleted by homologous recombination since it lies outside of the region of vector homology with the mouse Igk locus. Colonies of drug-resistant ES cells are physically extracted from their plates after they became visible to the naked eye about a week later. These picked colonies are disaggregated, re-plated in micro-well plates, and cultured for several days. Thereafter, each of the clones of cells is divided such that some of the cells could be frozen as an archive, and the rest used for isolation of DNA for analytical purposes.

DNA from the ES cell clones is screened by PCR using a widely used gene-targeting assay design. For this assay, one of the PCR oligonucleotide primer sequences maps outside the region of identity shared between the 3' vector (905) and the genomic DNA (901), while the other maps within the novel DNA between the two arms of genomic identity in the vector, i.e., in the HPRT (945) or neo (947) genes. According to the standard design, these assays detect pieces of DNA that are only present in clones of ES cells derived from transfected cells that had undergone fully legitimate homologous recombination between the 3' vector (905) and the endogenous mouse Igk locus. Two separate transfections are performed with the 3' vector (905). PCR-positive clones from the two transfections are selected for expansion followed by further analysis using Southern blot assays.

The Southern blot assays are performed according to widely used procedures; they involve three probes and genomic DNA digested with multiple restriction enzymes chosen so that the combination of probes and digests allowed for conclusions to be drawn about the structure of the targeted locus in the clones and whether it is properly modified by homologous recombination. One of the probes maps to DNA sequence flanking the 5' side of the region of identity shared between the 3' kappa targeting vector (905) and the genomic DNA; a second probe also maps outside the region of identity but on the 3' side; the third probe maps within the novel DNA between the two arms of genomic identity in the vector, i.e., in the HPRT (945) or neomycin resistance (947) genes. The Southern blot identifies the presence of the expected restriction enzyme-generated fragment of DNA corresponding to the correctly mutated, i.e., by homologous recombination with the 3' kappa targeting vector (905) part of the kappa locus as detected by one of the external probes and by the neomycin resistance or HPRT gene probe. The external probe detects the mutant fragment and also a wild-type fragment from the non-mutant copy of the immunoglobulin kappa locus on the homologous chromosome.

Karyotypes of PCR- and Southern blot-positive clones of ES cells are analyzed using an in situ fluorescence hybridization procedure designed to distinguish the most commonly arising chromosomal aberrations that arise in mouse ES cells. Clones with such aberrations are excluded from further use. Karyoptypically normal clones that are judged to have the expected correct genomic structure based on the Southern blot data are selected for further use.

Acceptable clones are then modified with the 5' vector (903) using procedures and screening assays that are essentially identical in design to those used with the 3' vector (905), except that puromycin selection is used instead of G418/neomycin selection, and the protocols are tailored to match the genomic region modified by the 5' vector (903). The goal of the 5' vector (903) transfection experiments is to isolate clones of ES cells that have been mutated in the expected fashion by both the 3' vector (905) and the 5' vector (903), i.e., doubly targeted cells carrying both engineered mutations. In these clones, the Cre recombinase causes a recombination (902) to occur between the loxP sites introduced into the kappa locus by the two vectors, resulting in a genomic DNA configuration shown at (907).

Further, the clones must have undergone gene targeting on the same chromosome, as opposed to homologous chromosomes, i.e., the engineered mutations created by the targeting vectors must be in cis on the same DNA strand rather than in trans on separate homologous DNA strands. Clones with the cis arrangement are distinguished from those with the trans arrangement by analytical procedures such as fluorescence in situ hybridization of metaphase spreads using probes that hybridize to the novel DNA present in the two gene targeting vectors (903 and 905) between their arms of genomic identity. The two types of clones can also be distinguished from one another by transfecting them with a vector expressing the Cre recombinase, which deletes the pu-Tk (939), HPRT (945) and neomycin resistance (947) genes if the targeting vectors have been integrated in cis, and comparing the number of colonies that survive ganciclovir selection against the thymidine kinase gene introduced by the 5' vector (903) and by analyzing the drug resistance phenotype of the surviving clones by a "sibling selection" screening procedure in which some of the cells from the clone are tested for resistance to puromycin or G418/neomycin. Cells with the cis arrangement of mutations are expected to yield approximately $10^3$ more ganciclovir-resistant clones than cells with the trans arrangement. The majority of the resulting cis-derived ganciclovir-resistant clones should also be sensitive to both puromycin and G418/neomycin, in contrast to the trans-derived ganciclovir-resistant clones, which should retain resistance to both drugs. Clones of cells with the cis-arrangement of engineered mutations in the kappa chain locus are selected for further use.

The doubly targeted clones of cells are transiently transfected with a vector expressing the Cre recombinase (902) and the transfected cells are subsequently placed under ganciclovir selection, as in the analytical experiment summarized above. Ganciclovir-resistant clones of cells are isolated and analyzed by PCR and Southern blot for the presence of the expected deletion (907) between the two engineered mutations created by the 5' vector (903) and the 3' vector (905). In these clones, the Cre recombinase has caused a recombination to occur between the loxP sites (937) introduced into the kappa chain locus by the two vectors. Because the loxP sites are arranged in the same relative orientations in the two vectors, recombination results in excision of a circle of DNA comprising the entire genomic interval between the two loxP sites. The circle does not contain an origin of replication and thus is not replicated during mitosis and is therefore lost from the clones of cells as they undergo clonal expansion. The resulting clones carry a deletion of the DNA that was originally between the two loxP sites. Clones that have the expected deletion are selected for further use.

The ES cell clones carrying the deletion of sequence in one of the two homologous copies of their immunoglobulin kappa chain locus are retransfected (904) with a Cre recombinase expression vector together with a piece of DNA (909) comprising a partly bovine immunoglobulin kappa chain locus containing Vκ (951) and Jκ (955) gene segments. The key features of this piece of DNA (referred to as "K-K") are the following: a lox5171 site (931); a neomycin resistance gene open reading frame (947) lacking the initiator methionine codon, but in-frame and contiguous with an uninterrupted open reading frame in the lox5171 site (931); a FRT site (927); an array of 8 bovine Vκ gene segments (951), each comprised of bovine coding sequences embedded in mouse noncoding sequences; optionally a 13.5 Kb piece of genomic DNA from immediately upstream of the cluster of J kappa region gene segments in the mouse kappa chain locus (not shown); a 2 Kb piece of DNA containing the 3 bovine Jκ region gene segments (955) embedded in mouse noncoding DNA; a loxP site (937) in opposite relative orientation to the lox5171 site (931).

The sequences of the bovine Vκ and Jκ gene coding regions are in Table 2.

In a second independent experiment, an alternative piece of partly bovine DNA (909) is used in place of the K-K DNA. The key features of this DNA (referred to as "L-K") are the following: a lox5171 site (931); a neomycin resistance gene open reading frame (947) lacking the initiator methionine codon, but in-frame and contiguous with an uninterrupted open reading frame in the lox5171 site (931); a FRT site (927); an array of 25 bovine lambda variable region gene segments (951), each comprised of bovine coding sequences embedded in mouse noncoding regulatory or scaffold sequences; optionally a 13.5 Kb piece of genomic DNA from immediately upstream of the cluster of J region gene segments in the mouse kappa chain locus (not shown); a 2 Kb piece of DNA containing the bovine Jλ, region gene segments embedded in mouse noncoding DNA (955); a loxP site (937) in opposite relative orientation to the lox5171 site (931).

The transfected clones from the K-K and L-K transfection experiments are placed under G418 selection, which enriches for clones of cells that have undergone a RMCE process in which the partly bovine donor DNA (909) is integrated in its entirety into the deleted immunoglobulin kappa chain locus between the lox5171 (931) and loxP (927) sites that are placed there by 5' (903) and 3' (905) vectors, respectively. Only cells that have properly undergone RMCE have the capability to express the neomycin resistance gene (947) because the promoter (929) as well as the initiator methionine codon (935) required for its expression are not present in the vector (909) and are already pre-existing in the host cell Igh locus (907). The DNA region created using the K-K sequence is illustrated at 911. The remaining elements from the 5' vector (903) are removed via Flp-mediated recombination (906) in vitro or in vivo, as described in [000138], resulting in the final bovine-based light chain locus as shown at 913.

G418-resistant ES cell clones are analyzed by PCR and Southern blot to determine if they have undergone the expected RMCE process without unwanted rearrangements or deletions. Both K-K and L-K clones that have the expected genomic structure are selected for further use.

The K-K ES cell clones and the L-K ES cell clones carrying the partly bovine immunoglobulin DNA in the mouse kappa chain locus (913), are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice for use in the mating are of the C57B1/6NTac strain, and also carry a transgene encoding the Flp recombinase that is expressed in their germline. Offspring from these matings are analyzed for the presence of the partly bovine immunoglobulin kappa or lambda light chain locus, and for loss of the FRT-flanked neomycin resistance gene that was created in the RMCE step. Mice that carry the partly bovine locus are used to establish colonies of K-K and L-K mice.

Mice carrying the partly bovine heavy chain locus, produced as described in Example 3, can be bred with mice carrying a bovine-based kappa chain locus. Their offspring are in turn bred together in a scheme that ultimately produces mice that are homozygous for both bovine-based loci, i.e., bovine-based for heavy chain and kappa light chain. Such mice produce partly bovine heavy chains comprised of bovine variable domains and mouse constant domains. They also produce partly bovine kappa proteins comprised of bovine kappa variable domains and the mouse kappa constant domain from their kappa loci. Monoclonal antibodies recovered from these mice are comprised of bovine heavy chain variable domains paired with bovine kappa variable domains.

A variation on the breeding scheme involves generating mice that are homozygous for the bovine-based heavy chain locus, but heterozygous at the kappa locus such that on one chromosome they have the K-K bovine-based locus and on the other chromosome they have the L-K bovine-based locus. Such mice produce partly bovine heavy chains comprised of bovine variable domains and mouse constant domains. They also produce partly bovine kappa proteins comprised of bovine kappa variable domains and the mouse kappa constant domain from one of their kappa loci. From the other kappa locus, they produce partly bovine lambda proteins comprised of bovine lambda variable domains the mouse kappa constant domain. Monoclonal antibodies recovered from these mice are comprised of bovine variable domains paired in some cases with bovine kappa variable domains and in other cases with bovine lambda variable domains.

Figure 10:
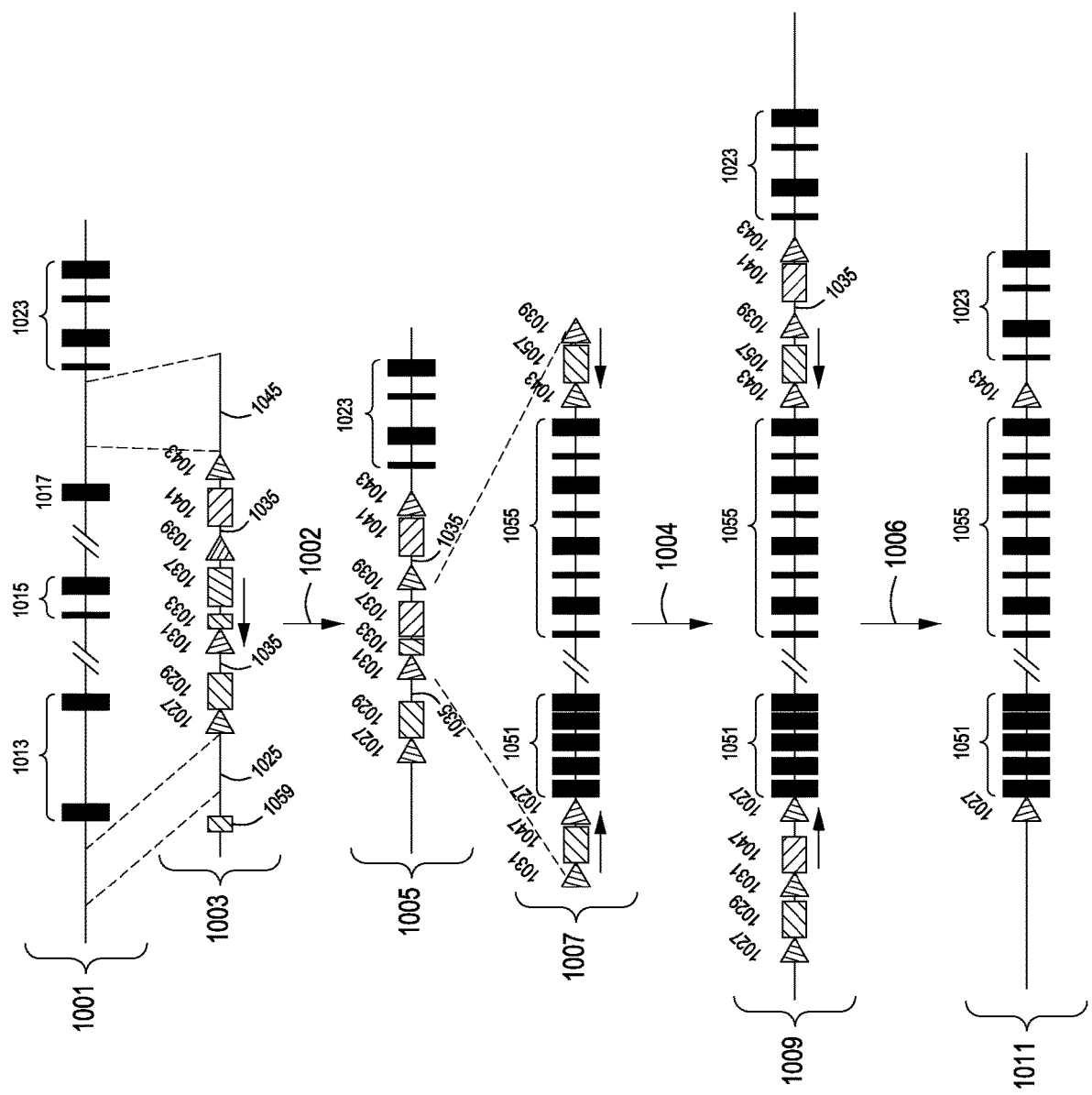
FIG. 10 is a schematic diagram illustrating the introduction of an engineered, partly bovine immunoglobulin λ L chain variable region gene locus into the endogenous immunoglobulin λ L chain locus of the mouse genome.

Example 5: Introduction of an Engineered, Partly Bovine Immunoglobulin Locus into the Immunoglobulin Lambda Chain Gene Locus of a Mouse Genome Another method for replacing a portion of a mouse genome with an engineered, partly bovine immunoglobulin locus is illustrated in FIG. 10. This method comprises deleting approximately 194 Kb of DNA from the wild-type mouse immunoglobulin lambda locus (1001)—comprising Vλx/Vλ2 gene segments (1013), Jλ2/Cλ2 gene cluster (1015), and Vλ1 gene segment (1017)—by a homologous recombination process involving a targeting vector (1003) that shares identity with the locus both upstream of the Vλx/Vλ2 gene segment (1013) and downstream of the Vλ1 gene segment (1017) in the immediate vicinity of the J3, C3, J1 and C1 lambda gene cluster (1023). The vector replaces the 194 Kb of DNA with elements designed to permit a subsequent site-specific recombination in which a non-native piece of DNA is moved into the modified Vλ, locus via RMCE (1004). In this example, the non-native DNA is a synthetic nucleic acid comprising both bovine and mouse sequences.

The key features of the gene targeting vector (1003) for accomplishing the 194 Kb deletion are as follows: a negative selection gene such as a gene encoding the A subunit of the diphtheria toxin (DTA, 1059) or a herpes simplex virus thymidine kinase gene (not shown); 4 Kb of genomic DNA from 5' of the mouse Vλx/Vλ2 variable region gene segment in the lambda locus (1025); a FRT site (1027); a piece of genomic DNA containing the mouse Polr2a gene promoter (1029); a translation initiation sequence (methionine codon embedded in a "Kozak" consensus sequence) (1035); a mutated loxP recognition sequence (lox5171) for the Cre recombinase (1031); a transcription termination/polyadenylation sequence (1033); an open reading frame encoding a protein that confers resistance to puromycin 1037), whereas this open reading frame is on the antisense strand relative to the Polr2a promoter and the translation initiation sequence next to it and is followed by its own transcription termination/polyadenylation sequence (1033); a loxP recognition sequence for the Cre recombinase (1039); a translation initiation sequence (a methionine codon embedded in a "Kozak" consensus sequence) (1033) on the same, antisense strand as the puromycin resistance gene open reading frame; a chicken beta actin promoter and cytomegalovirus early enhancer element (1041) oriented such that it directs transcription of the puromycin resistance open reading frame, with translation initiating at the initiation codon downstream of the loxP site and continuing back through the loxP site into the puromycin open reading frame all on the antisense strand relative to the Polr2a promoter and the translation initiation sequence next to it; a mutated recognition site for the Flp recombinase known as an "F3" site 1043).

Mouse embryonic stem (ES) cells derived from C57B1/6NTac mice are transfected (1002) by electroporation with the targeting vector (1003) according to widely used procedures. Homologous recombination replaces the native DNA with the sequences from the targeting vector (1003) in the 196 Kb region resulting in the genomic DNA configuration depicted at 1005.

Prior to electroporation, the vector DNA is linearized with a rare-cutting restriction enzyme that cuts only in the prokaryotic plasmid sequence or the polylinker associated with it. The transfected cells are plated and after ~24 hours placed under positive drug selection using puromycin. There is also negative selection for cells that have integrated the vector into their DNA but not by homologous recombination. Non-homologous recombination will result in retention of the DTA genes, which will kill the cells when the genes are expressed, whereas the DTA genes are deleted by homologous recombination since they lie outside of the region of vector homology with the mouse Igl locus. Colonies of drug-resistant ES cells are physically extracted from their plates after they became visible to the naked eye over a week later. These picked colonies are disaggregated, re-plated in micro-well plates, and cultured for several days. Thereafter, each of the clones of cells are divided such that some of the cells are frozen as an archive, and the rest used for isolation of DNA for analytical purposes.

DNA from the ES cell clones is screened by PCR using a widely used gene-targeting assay design. For these assays, one of the PCR oligonucleotide primer sequences maps outside the regions of identity shared between the targeting vector and the genomic DNA, while the other maps within the novel DNA between the two arms of genomic identity in the vector, e.g., in the puro gene (1037)). According to the standard design, these assays detect pieces of DNA that would only be present in clones of cells derived from transfected cells that had undergone fully legitimate homologous recombination between the targeting vector (1003) and the native DNA (1001).

Six PCR-positive clones from the transfection (1002) are selected for expansion followed by further analysis using Southern blot assays. The Southern blots involve three probes and genomic DNA from the clones that has been digested with multiple restriction enzymes chosen so that the combination of probes and digests allow identification of whether the ES cell DNA has been properly modified by homologous recombination.

Karyotypes of the six PCR- and Southern blot-positive clones of ES cells are analyzed using an in situ fluorescence hybridization procedure designed to distinguish the most commonly arising chromosomal aberrations that arise in mouse ES cells. Clones that show evidence of aberrations are excluded from further use. Karyoptypically normal clones that are judged to have the expected correct genomic structure based on the Southern blot data are selected for further use.

The ES cell clones carrying the deletion in one of the two homologous copies of their immunoglobulin lambda chain locus are retransfected (1004) with a Cre recombinase expression vector together with a piece of DNA (1007) comprising a partly bovine immunoglobulin lambda chain locus containing V, J and C region gene segments. The key features of this piece of DNA 1007 are as follows: a lox5171 site (1031); a neomycin resistance gene open reading frame lacking the initiator methionine codon, but in-frame and contiguous with an uninterrupted open reading frame in the lox5171 site (1047); a FRT site (1027); an array of 25 bovine lambda variable region gene segments, each comprised of bovine lambda coding sequences embedded in mouse lambda noncoding sequences (1051); an array of J-C units where each unit is comprised of a bovine J$\lambda$, gene segment and a mouse lambda constant domain gene segment embedded within noncoding sequences from the mouse lambda locus (1055) (the bovine J$\lambda$, gene segments are those encoding J1, J2, J6 and J7, while the mouse lambda constant domain gene segments are C1 and/or C2 and/or C3); a mutated recognition site for the Flp recombinase known as an "F3" site (1043); an open reading frame conferring hygromycin resistance (1057), which is located on the antisense strand relative to the immunoglobulin gene segment coding information in the construct; a loxP site (1029) in opposite relative orientation to the lox5171 (1031) site.

The sequences of the bovine V$\lambda$, and A gene coding regions are in Table 3.

The transfected clones are placed under G418 and/or hygromycin selection, which enriches for clones of cells that have undergone a RMCE process in which the partly bovine donor DNA is integrated in its entirety into the deleted immunoglobulin lambda chain locus between the lox5171 and loxP sites that were placed there by the gene targeting vector. The remaining elements from the targeting vector (1003) are removed via FLP-mediated recombination (1006) in vitro or in vivo (described in [000152]) resulting in the final bovinized locus as shown at 1011.

G418/hygromycin-resistant ES cell clones are analyzed by PCR and Southern blot to determine if they have undergone the expected recombinase-mediated cassette exchange process without unwanted rearrangements or deletions. Clones that have the expected genomic structure are selected for further use.

The ES cell clones carrying the partly bovine immunoglobulin DNA (1011) in the mouse lambda chain locus are microinjected into mouse blastocysts from strain DBA/2 to create partially ES cell-derived chimeric mice according to standard procedures. Male chimeric mice with the highest levels of ES cell-derived contribution to their coats are selected for mating to female mice. The female mice of choice here are of the C57B1/6NTac strain, which carry a transgene encoding the Flp recombinase expressed in their germline. Offspring from these matings are analyzed for the presence of the partly bovine immunoglobulin lambda chain locus, and for loss of the FRT-flanked neomycin resistance gene and the F3-flanked hygromycin resistance gene that were created in the RMCE step. Mice that carry the partly bovine locus are used to establish a colony of mice.

In some aspects, the mice comprising the bovine-based heavy chain and kappa locus (as described in Examples 3 and 4) are bred to mice that carry the bovine-based lambda locus. Mice generated from this type of breeding scheme are homozygous for the bovine-based heavy chain locus, and can be homozygous for the K-K bovine-based locus or the L-K bovine-based locus. Alternatively, they can be heterozygous at the kappa locus carrying the K-K locus on one chromosome and the L-K locus on the other chromosome. Each of these mouse strains are homozygous for the bovine-based lambda locus. Monoclonal antibodies recovered from these mice are comprised of bovine heavy chain variable domains paired in some cases with bovine kappa variable domains and in other cases with bovine lambda variable domains. The lambda variable domains are derived from either the bovine-based L-K locus or the bovine-based lambda locus.

Figure 11:
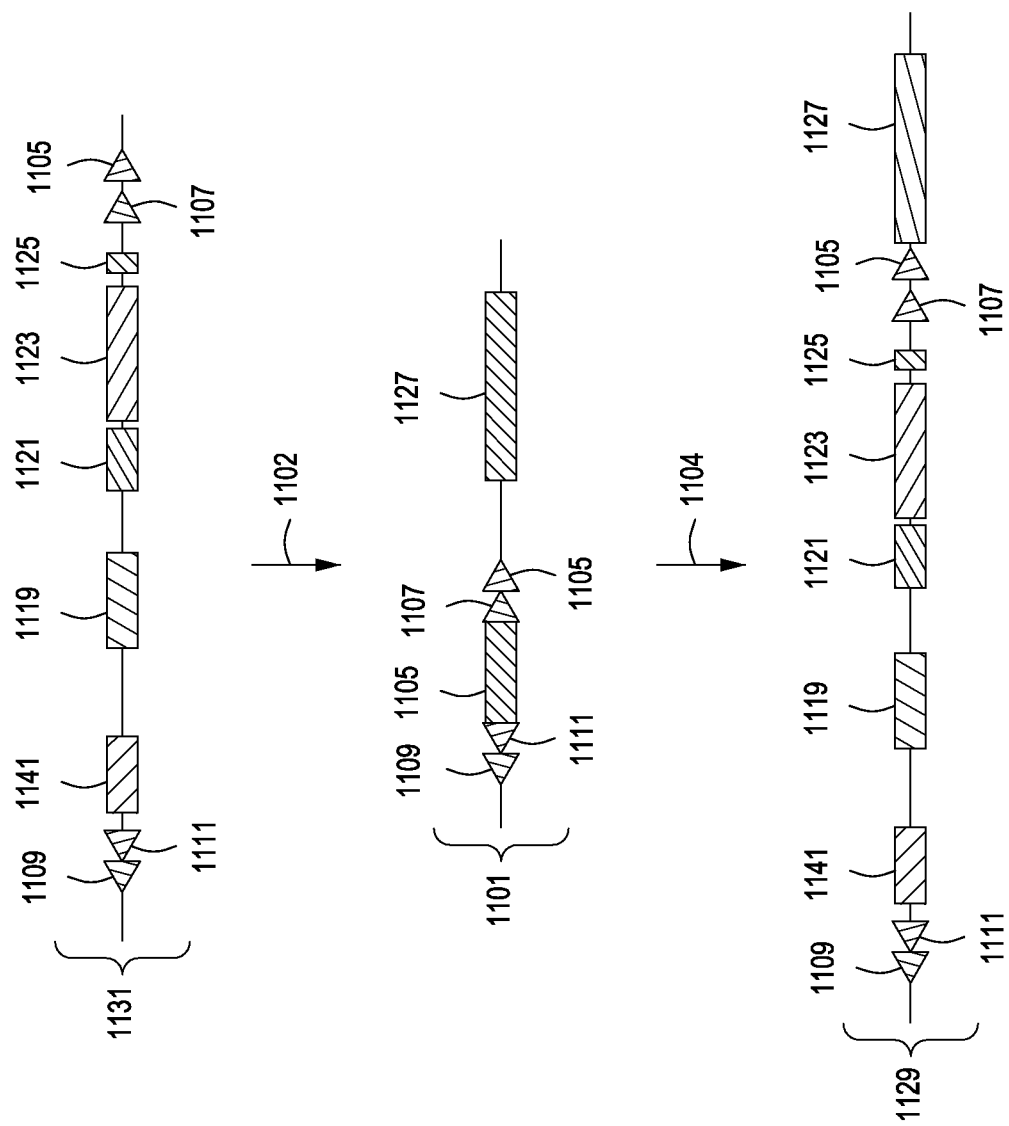
FIG. 11 is a schematic diagram illustrating the introduction of an engineered, partly bovine immunoglobulin locus comprising a bovine $V_H$ minilocus via RMCE.

Example 6: Introduction of an Engineered, Partly Bovine Immunoglobulin Minilocus into a Mouse Genome In certain other aspects, the partly bovine immunoglobulin locus comprises a bovine variable domain minilocus such as the one illustrated in FIG. 11. Here instead of a partly bovine immunoglobulin locus comprising all or substantially all of the bovine $V_H$ gene segment coding sequences, the mouse immunoglobulin locus is replaced with a minilocus (1119) comprising fewer chimeric bovine $V_H$ gene segments, e.g. 1-20 bovine $V_H$ gene segments determined to be functional; that is, not pseudogenes.

A site-specific targeting vector (1131) comprising the partly bovine immunoglobulin locus to be integrated to the mammalian host genome is introduced (1102) into the genomic region (1101) with the deleted endogenous immunoglobulin locus comprising the puro-TK gene (1105) and the following flanking sequence-specific recombination sites: mutant FRT site (1109), mutant LoxP site (1111), wild-type FRT site (1107), and wild-type LoxP site (1105). The site-specific targeting vector comprises i) an array of optional PAIR elements (1141, see [00069]); ii) a VH locus (1119) comprising, e.g., 1-20 bovine VH coding regions and intervening sequences based on the mouse genome endogenous sequences; iii) a 21.6 kb pre-D region (1121) comprising mouse sequence; iv) a DH locus (1123) and a JH locus (1125) comprising 10 DH and 4 JH bovine coding sequences and intervening sequences based on the mouse genome endogenous sequences The partly bovine immunoglobulin locus is flanked by recombination sites-mutant FRT (1109), mutant LoxP (1111), wild-type FRT (1107), and wild-type LoxP (1105)—that allow recombination with the modified endogenous locus. Upon introduction of the appropriate recombinase (e.g., Cre) (1104), the partly bovine immunoglobulin locus is integrated into the genome upstream of the constant gene region (1127) as shown at 1129.

As described in Example 1, the primary screening for introduction of the partly bovine immunoglobulin variable region locus is carried out by primary PCR screens supported by secondary Southern blotting assays. The deletion of the puro-TK gene (1105) as part of the recombination event allows identification of the cells that did not undergo the recombination event using ganciclovir negative selection.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. In the claims that follow, unless the term "means" is used, none of the features or elements recited therein should be construed as means-plus-function limitations pursuant to 35 U.S.C. § 112¶6. All references cited in the application are to be incorporated by reference in their entirety for all purposes.

TABLE 1

Bovine Igh sequence information

| FUNCTIONALITY | GENE NAME | GenBank Accession Number | Source | Comments |
|---|---|---|---|---|
| F | IGHV4-pB7S2 | U36823 | T | |
| F | IGHV4-pBSS1 | U36824 | T | |
| F | IGHV4-p2C7.5 | AF000012 | T | |
| F | IGHV4-p4H9.1 | AF000013 | T | |
| F | IGHV4-p5H4.1 | AF000014 | T | |
| F | IGHV4-p7B7.2 | AF000015 | T | |
| F | IGHV4-p7G1.5 | AF000016 | T | |
| F | IGHV4-1H12 | AF015506 | T | Preferential use in ultralong CDRH3 Ab |
| F | IGHV4-A7M | U49772 | T | |
| F | IGHV4-A10M | U49773 | T | |
| F | IGHV4-PUC13.8.75 | X62916 | T | |
| F | IGHDH1 | AY559838.1 | G | |
| F | IGHDH2 | AY559839.1 | G | Ultralong DH used in ultralong CDRH3 Ab |
| F | IGHDH4 | | G | |
| ? | IGHDHQ52 | AY149283 | G | Appears functional but not expressed |
| F | IGHJH1 | AY158087 | G | |
| P | IGHJH12 | AY158087 | G | |
| P | IGHJHPSI | AY158087 | G | |
| P | IGHJHPS2 | AY158087 | G | |
| P | IGHJHPS3 | AY158087 | G | |
| P | IGHJHPS4 | AY158087 | G | |

F, functional; P, pseudogene; ?, Unknown; T, transcript; G, genomic.

TABLE 2

Bovine Ig kappa sequence information
From version 3.1 of the *Bos tarus* genome sequence. Modified from Ekman, et al., BMC Immunology 10:22 (2009). (NB, the sequence and annotation of the cow genome is still incomplete. This table does not necessarily describe the complete bovine VK and JK gene repertoire.)
P, pseudogene; F, functional; ORF, open reading frame. The 7mer-spacer-9mer comprises the RSS required for V→J recombination. Variations in the heptamer sequence that are likely to prevent VJ recombination are underlined.

| FUNCTION-ALITY | GENE NAME | SCAFFOLD | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|
| P | IGKV3 | Chr11.003.53 | 1331507 | + | 48 | + | 385 | CACAGTG | 12 | ACATAAACC |
| P | IGKV7 | Chr11.003.53 | 1365060 | + | 49 | gc/ag | 389 | CACAGTG | 12 | ACATAAGCC |
| P | IGKV9 | Chr11.003.53 | 1387606 | + | 47 | + | 389 | CACAGTG | 12 | ACATAAACC |
| P | IGKV12 | Chr11.003.53 | 1422986 | + | 47 | gt/aa | 390 | CACAGTG | 12 | ACATAAACC |

TABLE 2-continued

Bovine Ig kappa sequence information
From version 3.1 of the *Bos tarus* genome sequence. Modified from Ekman, et al., BMC Immunology 10:22 (2009). (NB, the sequence and annotation of the cow genome is still incomplete. This table does not necessarily describe the complete bovine VK and JK gene repertoire.)
P, pseudogene; F, functional; ORF, open reading frame. The 7mer-spacer-9mer comprises the RSS required for V→J recombination. Variations in the heptamer sequence that are likely to prevent VJ recombination are underlined.

| FUNCTION-ALITY | GENE NAME | SCAFFOLD | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|
| P | IGKV15 | Chr11.003.53 | 1447022 | + | 47 | + | 389 | CACAGTG | 12 | ACATAAACC |
| P | IGKV18 | Chr11.003.53 | 1483551 | + | 47 | at/ag | 388 | TACAGTG | 12 | ACATAAACC |
| P | IGKV20 | Chr11.003.53 | 1497328 | + | 47 | + | 396 | CACAGTG | 12 | ACATAAACC |
| F | IGKV8 | Chr11.003.53 | 1379686 | + | 49 | + | 414 | CACAGTG | 12 | ACACAAACC |
| F | IGKV10 | Chr11.003.53 | 1398842 | + | 49 | + | 402 | CACAGTG | 12 | ACACAAACC |
| F | IGKV11 | Chr11.003.53 | 1415920 | + | 49 | + | 414 | CACAGTG | 12 | ACACAAACC |
| F | IGKV13 | Chr11.003.53 | 1433551 | + | 49 | + | 402 | CACAGTG | 12 | ACACAAACC |
| F | IGKV14 | Chr11.003.53 | 1439947 | + | 49 | + | 414 | CACAGTG | 12 | ACACAAACC |
| F | IGKV19 | Chr11.003.53 | 1490916 | + | 49 | + | 414 | CACAGTG | 12 | ACACAAACC |
| F | IGKV21 | Chr11.003.53 | 1508121 | + | 49 | + | 401 | CACAGTG | 12 | ACACAAACC |
| ORF | IGKV17 | Chr11.003.53 | 1475628 | + | 49 | + | 415 | CACAGTG | 12 | ACACAAACT |
| P | IGKV4 | Chr11.003.53 | 1350496 | + | 49 | + | 420 | CACAGTG | 12 | ACACAAACC |
| F | IGKV23 | Chr11.003.53 | 1523817 | + | 52 | + | 123 | CACAGTG | 12 | ACATAAACC |
| P | IGKV1 | Chr11.003.53 | 1306120 | + | 48 | + | 125 | CACAGTA | 12 | ACATAAACC |
| P | IGKV6 | Chr11.003.53 | 1356488 | + | 49 | ga/at | 125 | CACAGTG | 12 | ACATAAACC |
| P | IGKV22 | Chr11.003.53 | 1512669 | + | 52 | + | 115 | TACAGTG | 12 | ACATAAACC |
| P | IGKV24 | Chr11.003.53 | 1559198 | + | 49 | ga/gg | 125 | CACAGTG | 12 | ACATAGACC |
| P | IGKV2 | Chr11.003.53 | 1310260 | + | 49 | + | 674 | TCCAGTG | 12 | ACAAAAACC |
| F | IGKJ1 | Chr11.003.53 | 1568662 | | | gt/ | | GGTTTTTGT | 23 | TGTTGTG |
| ORF | IGKJ2 | Chr11.003.53 | 1568968 | | | gt/ | | GGTATTTGT | 22 | CACTGTG |
| F | IGKJ3 | Chr11.003.53 | 1569313 | | | gt/ | | GGTTTTTGT | 23 | CGCTGTG |
| F | IGKC1 | Chr11.003.53 | 1573163 | | | /ag | | | | |

TABLE 3

Bovine Ig lambda sequence information

From version 3.1 of the *Bos torus* genome sequence. Modified from Ekman, et al., BMC Immunology 10:22 (2009). (NB, the sequence and annotation of the cow genome is still incomplete. This table does not necessarily describe the complete bovine Vλ Jλ, and Tl gene repertoire.)
F, functional; P, pseudogene; ORF, open reading frame. The 7mer - spacer - 9mer are the RSS required for V→J recombination. Variations in the heptamer sequence and spacer length that are likely to prevent VJ recombination are underlined. The bovine lambda locus is on chromosome 17, but some of the sequences listed have not been mapped to a specific chromosome, "ChrUn".

| FUNTION-ALITY | GENE NAME | SCAFFOLD | ORIEN-TATION | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|---|
| F | IGLV2 | Chr17.003.79 | + | 7214 | + | 46 | + | 109 | CACAGTG | 23 | ACAAAAACC |
| F | IGLV6 | Chr17.003.79 | + | 31803 | + | 46 | + | 107 | CACAGTG | 23 | ACAAAAACC |
| F | IGLV8 | Chr17.003.79 | + | 51575 | + | 46 | + | 109 | CACAGTG | 23 | ACAAAAACC |
| F | IGLV23 | Chr17.003.82 | + | 176607 | + | 46 | + | 109 | CACAGTG | 23 | ACAAAAACC |
| F | IGLV25 | Chr17.003.82 | + | 188203 | + | 46 | + | 109 | CACAGTG | 23 | ACAAAAACC |
| F | IGLV27 | Chr17.003.82 | + | 199292 | + | 46 | + | 109 | CACAGTG | 22 | ACAAAAACC |
| F | IGLV28 | Chr17.003.82 | + | 205976 | + | 46 | + | 109 | CACAGTG | 22 | ACAAAAACC |
| F | IGLV30 | Chr17.003.82 | + | 217850 | + | 46 | + | 110 | CACAGTG | 23 | ACAAAAACC |
| F | IGLV33 | ChrUn.003.1470 | + | 11331 | + | 46 | + | 107 | CACAGTG | 22 | ACAAAAACC |
| F | IGLV35 | ChrUn.003.1470 | + | 23536 | + | 46 | + | 109 | CACAGTG | 23 | ACAAAAACC |
| F | IGLV37 | ChrUn.003.1470 | + | 28706 | + | 46 | + | 108 | CACAGTG | 22 | ACAAAAACC |
| F | IGLV39 | ChrUn.003.1470 | + | 40610 | + | 46 | + | 109 | CACAGTG | 23 | ACAAAAACC |
| F | IGLV43 | ChrUn.003.1470 | + | 64583 | + | 46 | + | 109 | CACAGTG | 23 | ACAAAAACC |
| F | IGLV45 | ChrUn.003.2253 | + | 1899 | + | 46 | + | 101 | CACAGTG | 23 | ACAAAAACC |
| F | IGLV49 | ChrUn.003.2253 | + | 25167 | + | 46 | + | 109 | CACAGTG | 23 | ACAAAAACC |
| F | IGLV55 | ChrUn.003.3961 | + | 9375 | + | 46 | + | 109 | CACAGTG | 23 | ACAAAAACC |
| FL | IGLV59 | ChrUn.003.4331 | - | 14640 | fragmented locus | | | | | | |
| ORF | IGLV20 | Chr17.003.82 | + | 167372 | + | 46 | + | 109 | CCCAGTG | 23 | ACAAAAACC |

TABLE 3-continued

Bovine Ig lambda sequence information

From version 3.1 of the *Bos torus* genome sequence. Modified from Ekman, et al., BMC Immunology 10:22 (2009). (NB, the sequence and annotation of the cow genome is still incomplete. This table does not necessarily describe the complete bovine Vλ Jλ, and Ti, gene repertoire.) F, functional; P, pseudogene; ORF, open reading frame. The 7mer - spacer - 9mer are the RSS required for V→J recombination. Variations in the heptamer sequence and spacer length that are likely to prevent VJ recombination are underlined. The bovine lambda locus is on chromosome 17, but some of the sequences listed have not been mapped to a specific chromosome, "ChrUn".

| FUNTION-ALITY | GENE NAME | SCAFFOLD | ORIEN-TATION | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|---|
| ORF | IGLV52 | ChrUn.003.2253 | + | 41583 | + | 46 | + | 109 | CACAGTG | 23 | ACAAAAACC |
| P | IGLV7 | Chr17.003.79 | + | 45009 | + | 46 | + | 109 | CACAGGG | 23 | ACAAAAACC |
| P | IGLV56 | ChrUn.003.3965 | + | 33 | fragm. locus | | -/aa | | CACAGTG | 23 | ACAAAAACC |
| F | IGLV10 | Chr17.003.79 | + | 138311 | + | 46 | + | 116 | CACAGTG | 24 | ACCAAAAACC |
| F | IGLV13 | Chr17.003.79 | + | 159555 | + | 46 | + | 115 | CACAGTG | 23 | ACAAAAACC |
| ORF | IGLV12 | Chr17.003.79 | + | 144619 | + | 46 | + | 117 | CGCAGTG | 23 | ACCGAAACC |
| P | IGLV11 | Chr17.003.79 | + | 141359 | + | 46 | + | 115 | CACAGTG | 23 | ACCACAACG |
| ORF | IGLV22 | Chr17.003.82 | + | 173177 | + | 46 | + | 110 | CACAGTG | 21 | ACAAAAACC |
| P | IGLV1 | Chr17.003.79 | + | 3906 | + | 46 | + | 109 | CACAGTG | 21 | ACAAAAAAC |
| P | IGLV4 | Chr17.003.79 | + | 17993 | - (ACG) | 46 | + | 109 | CACAGTG | 22 | ACAAAAACC |
| P | IGLV5 | Chr17.003.79 | + | 28230 | + | 46 | + | 109 | TACAGTG | 22 | ACAAAAACC |
| P | IGLV24 | Chr17.003.82 | + | 184889 | + | 46 | + | 109 | CACAGTG | 21 | ACAAAAACC |
| P | IGLV26 | Chr17.003.82 | + | 195999 | + | 46 | + | 109 | CACAGTG | 21 | ACAAAAACC |
| P | IGLV29 | Chr17.003.82 | + | 214561 | + | 46 | + | 109 | CACAGTG | 21 | ACAAAAACC |
| P | IGLV36 | ChrUn.003.1470 | + | 25135 | + | 46 | at/ag | 109 | TACAGTG | 22 | ACAAAAACC |
| P | IGLV38 | ChrUn.003.1470 | + | 37294 | + | 46 | + | 109 | CACAGTG | 21 | ACAAAAACC |
| P | IGLV42 | ChrUn.003.1470 | + | 60021 | + | 46 | + | 109 | CACAGTG | 21 | ACAAAAACC |
| P | IGLV48 | ChrUn.003.2253 | + | 21570 | + | 46 | + | 109 | CACAGTG | 21 | ACAAAAACC |
| P | IGLV54 | ChrUn.003.3961 | + | 6069 | + | 46 | + | 109 | CACAGTG | 21 | ACAAAAACC |

TABLE 3-continued

Bovine Ig lambda sequence information

From version 3.1 of the Bos torus genome sequence. Modified from Ekman, et al., BMC Immunology 10:22 (2009). (NB, the sequence and annotation of the cow genome is still incomplete. This table does not necessarily describe the complete bovine VλJλ, and Ti gene repertoire.)
F, functional; P, pseudogene; ORF, open reading frame. The 7mer - spacer - 9mer are the RSS required for V→J recombination. Variations in the heptamer sequence and spacer length that are likely to prevent VJ recombination are underlined. The bovine lambda locus is on chromosome 17, but some of the sequences listed have not been mapped to a specific chromosome, "ChrUn".

| FUNTION-ALITY | GENE NAME | SCAFFOLD | ORIEN-TATION | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|---|
| T | IGLV31 | ChrUn.003.14 | + | 818451 | truncated | | | | TACATTG | 22 | ACAAAAACC |
| F | IGLV14 | Chr17.003.79 | + | 170363 | + | 46 | + | 139 | CACAGTG | 23 | ACACAAACC |
| F | IGLV15 | Chr17.003.79 | + | 176830 | + | 46 | + | 155 | CACAGTG | 23 | ACACAAACC |
| F | IGLV16 | Chr17.003.79 | + | 189021 | + | 46 | + | 161 | CACAGTG | 23 | ACACAAACC |
| F | IGLV17 | Chr17.003.79 | + | 193750 | + | 45 | + | 138 | CACAGTG | 23 | ACACAAACC |
| F | IGLV18 | Chr17.003.79 | + | 197591 | + | 46 | + | 369 | CACAGTG | 22 | ATGCAAACC |
| F | IGLV21 | Chr17.003.82 | + | 170160 | + | 46 | + | 116 | CACGGAG | 23 | ACAGAAACC |
| F | IGLV9 | Chr17.003.79 | + | 54362 | + | 46 | + | 117 | CACGGCG | 23 | ACCTAAATC |
| P | IGLV19 | Chr17.003.82 | + | 162532 | + | 45 | gt/gg | 114 | — | — | — |
| P | IGLV60 | Chr17.003.79 | + | 49196 | - (GTG) | | | 114 | — | — | — |
| T | IGLV57 | ChrUn.003.3965 | + | 8445 | + | 46 | + | 116 | CACAGTG | 22 | ACAAAACCC |
| T | IGLV61 | ChrUn.003.2253 | + | 27669 | truncated | | | | — | — | — |
| T | IGLV63 | ChrUn.003.2253 | + | 44067 | truncated | | | | CACAGTG | 23 | ACGAGAGCC |
| F | IGLV40 | ChrUn.003.1470 | + | 47886 | + | 46 | + | 99 | CACAGAG | 23 | ACTGAACCC |
| F | IGLV46 | ChrUn.003.2253 | + | 8561 | + | 46 | + | 99 | CACAGTG | 23 | ACTGAACCC |
| F | IGLV3 | Chr17.003.79 | + | 15108 | + | 46 | + | 98 | CACAGTG | 23 | ACCAAAATC |
| P | IGLV32 | ChrUn.003.1470 | + | 7476 | + | 46 | + | 98 | CACAGTG | 23 | ACCAAAACC |
| P | IGLV34 | ChrUn.003.1470 | + | 19684 | + | 46 | + | 98 | CTGAGTG | 24 | AGCAAAACC |
| P | IGLV50 | ChrUn.003.2253 | + | 33606 | + | 45 | + | 99 | CACAGTG | 23 | ATTAAAACC |

TABLE 3-continued

Bovine Ig lambda sequence information

From version 3.1 of the *Bos torus* genome sequence. Modified from Ekman, et al., BMC Immunology 10:22 (2009). (NB, the sequence and annotation of the cow genome is still incomplete. This table does not necessarily describe the complete bovine VλJλ, and Ti gene repertoire.)
F, functional; P, pseudogene; ORF, open reading frame. The 7mer - spacer - 9mer are the RSS required for V→J recombination. Variations in the heptamer sequence and spacer length that are likely to prevent VJ recombination are underlined. The bovine lambda locus is on chromosome 17, but some of the sequences listed have not been mapped to a specific chromosome, "ChrUn".

| FUNCTION-ALITY | GENE NAME | SCAFFOLD | ORIEN-TATION | START OF SEQUENCE SIMILARITY TO IG KAPPA GENE | TRANS-LATION START (ATG) | EXON 1 LENGTH (bp) | SPLICE SIGNALS (gt/ag) | INTRON LENGTH (bp) | 7mer | spacer (bp) | 9mer |
|---|---|---|---|---|---|---|---|---|---|---|---|
| P | IGLV58 | ChrUn.003.3965 | + | 15306 | + | 46 | + | 99 | CACAGTG | 23 | ACCAAAACC |
| P | IGLV62 | ChrUn.003.2253 | + | 32163 | + | | | | fragmented locus | | |
| T | IGLV51 | ChrUn.003.2253 | + | 37981 | truncated | | | 99 | | | |
| P | IGLV44 | ChrUn.003.1470 | + | 72903 | + | 49 | + | 111 | CGCAGTG | 23 | ACAAACACC |
| ORF | IGLV41 | ChrUn.003.1470 | + | 54319 | + | 46 | + | 130 | CACAGTG | 19 | ACAAAAACC |
| ORF | IGLV53 | ChrUn.003.3961 | + | 369 | + | 46 | + | 130 | CGCGGTG | 22 | ACAAAAACC |
| P | IGLV47 | ChrUn.003.2253 | + | 15795 | + | 46 | + | 161 | CGCGGTG | 22 | ACAAAAACC |
| F | IGLJ2 | Chr17.003.79 | + | 224120 | | | gt/ | | CGCGGTG | 22 | ACGAAAACC |
| F | IGLJ3 | Chr17.003.79 | + | 230438 | | | gt/ | | GGTTTTTGT | 12 | CACTGTG |
| ORF | IGLJ4 | Chr17.003.79 | + | 236715 | | | gt/ | | GGTTTTTGT | 12 | CACTGTG |
| F | IGLC1 | Chr17.003.79 | + | 219204 | | | /ag | | GGTTTTTGT | 12 | CACTGTG |
| F | IGLC2 | Chr17.003.79 | + | 225462 | | | /ag | | | | |
| F | IGLC3 | Chr17.003.79 | + | 231771 | | | /ag | | | | |
| P | IGLC4 | Chr17.003.79 | + | 238040 | | | /ag | | | | |
| P | IGLC5 | ChrUn.003.11775 | + | 1218 | | | /gg | | | | |

TABLE 4

Miscellaneous sequence data.

A. Pre-DJ
This is a 21609 bp fragment upstream of the Ighd-5 DH gene. The pre-DJ sequence can be found in *Mus musculus* strain C5713E16,1 chromosome 12, Assembly: GRCm38.p4, Annotation release 106, Sequence ID: NC_000078.6
The entire sequence lies between the two 100 bp sequences shown below:
Upstream of the Ighd-5 DH gene segment, corresponding to positions 113526905-113527004 in NC_000078.6:

ATTTCTGTACCTGATCTATGTCAATATCTGTACCATGGCTCTAGCAGAGATGAAATATGAGAC
AGTCTGATGTCATGTGGCCATGCCTGGTCCAGACTTG (SEQ ID NO. 1)

2 kb upstream of the Adam6a gene corresponding to positions 113548415-113548514 in NC_000078.6:
GTCAATCAGCAGAAATCCATCATACATGAGACAAAGTTATAATCAAGAAATGTTGCCCATAG
GAAACAGAGGATATCTCTAGCACTCAGAGACTGAGCAC (SEQ ID NO, 2)

B. Adam6a
Adam6a (a disintegrin and metallopeptidase domain 6A) is a gene involved in male fertility. The Adam6a sequence can be found in *Mus musculus* strain C57B136,1 chromosome 12, Assembly: GRCm38.1)4, Annotation release 106, Sequence ID: NC_000078.6 at position 113543908-113546414.
Adam6a sequence ID: OTTMUSG00000051592 (VEGA)

TABLE 5

Chimeric bovine/mouse Ig gene sequences.

Igk Version A
Sequence upstream of mouse Igkv 1-133 (SEQ ID No. 3):
GCATTGAATAAACCAGTATAAACAAGCAAGCAAAGATAGATAGATAGATAGATAGATAGA
TAGATAGATACATAGATAGATAGATAGATAGATAGATGATAGATAGATAGATAGATAGATAG
ATTTTTACGTATAATACAATAAAAACATTCATTGTCCCTCTATTGGTGACTACTCAAGGAAA
AAATGTTCATATGCAAGAAAAAATGTTATCATTACCAGATGATCCAGCAATCTAGCAATATAT
ATATTGTTTATTCACAAAACATGAATGAACCTTTTAAGAAGCTGTTACAGTGTAAAAATTAAG
TTAAATCACTGAAGAACATATACTGTGTGATTTCATTCAAATGAAATTTGAGAAGTAAATATA
TATGTATATATATATATATGTAAAAAATATAAGTCTGAACTACAAAATTCAATTTGTTTGAT
ATGTAAGAATAAGAAAAATTGACCCCCAAAATTTGTTAATAATTAGGTATGTGTATTTTTATG
AATATATAAGTATAATAATGCTTATAGTATACACTATTCTGAATCACATTTATTCCCTAAGTGT
GTTCCCTTGATTATAATTAAAAGTATATTTTTAAATACAGAGTCAGAGTACAGTCAATAAGG
CGAAAATATAGTTGAATGATTTGCTTCAGCTTTTGTAATGTACTAGAGATTGTGAGTACAAAG
TCTCAGAGCTCATTTTATCCCTGACAATAACCAGCTCTGTGCTTCAAGTACATTTCCATCTTTC
TCTGAAATTTAGTCTTATATAGATAGACAAAATTTAAGTAAATTTCAAACTACACAGAACAAC
TAAGTTGTTGTTTCATATTGATAATGGATTTGAACTGCATTAACAGAACTTTAACATCCTGCTT
ATTCTCCCTTCAGCCATCATATTTTGCTTTATTATTTTCACTTTTTGAGTTATTTTTCACATTCAG
AAAGCTCACATAATTGTCACTTCTTTGTATACTGGTATACAGACCAGAACATTTGTATATTGTT
CCCTGGGGAGGTCTTTGCCCTGTTGGCCTGAGATAAAACCTCAAGTGTCCTCTTGCCTCCACTG
ATCACTCTCCTATGTTTATTTCCTCAAA Cow exon 1 (leader) from LOC100294952 (SEQ ID No. 4):
Atgagattctctgctcagctcctggggctcctcctgctctgggtcccag Cow intron 1 from LOC100294952 (SEQ ID No. 5):
Gtaagtacagagagggatgagaaggaggatggggggtgagttctggggcagcactgctctc-
cacatgtgttctctgttagatgtgtatgacttgtcc
tgcagatgagcatgggaaccttagatcaatgatagtgaggaatgttcca-
gaaggaagaaggtcctgtgctctggtcaggactgtgacaggggaagt
ggggatgatgtaggggatgtttagaggtctctttatacttcacagatatcaagttcatt-
attgtgattgtacaattttgctgtatgatcacagaca
atgtgagtaatacaaagtagtatt aatgttttagctaaaataaatcagaaaatggaaacaataaaaatggttgctaatatttg-
tagctttctaat
tctctgtcattcctttag Cow Vκ from LOC100294952 (SEQ ID No. 6):
Gatccagtggggatgttgtgctgacccagactccactctccctgtctatcatccctgga-
gagatggcctccatctcctgcaagtctagtcagagcc
tggtacacagtgatggaaaaacctatttgaattggattcaatataaaccaggccaatcac-
cacagggtctgatctatcaggtttccaaccgttact
ctggggtctcagacaggttcactggcagtgggtcagggacagatttcacacttacaatca-
gcagagtgcaggctgaggatgctggagtctattact
gttaccaaggtacagaagat Mouse RSS heptamer
CACAGTG Mouse sequence downstream of RSS heptamer (SEQ ID No. 7):
ATACAGACTCTATCAAAAACTTCCTTGCCTGGGGCAGCCCAGCTGACAATGTGCAATCTGAAG
AGGAGCAGAGAGACATCTTGTGTCTGTGTGAGAAGGAGGGGCTGGGATACATGAGTAATTCTT
TGCAGCTGTGAGCTCTG

TABLE 5-continued

Chimeric bovine/mouse Ig gene sequences.

Igk Version B
Sequence upstream of mouse Igkv 1-133 (SEQ ID No. 8):
GCATTGAATAAACCAGTATAAACAAGCAAGCAAAGATAGATAGATAGATAGATAGATA
GATAGATACATAGATAGATAGATAGATAGATGATAGATAGATAGATAGATAGATAGAT
TTTTACGTATAATACAATAAAAACATTCATTGTCCCTCTATTGGTGACTACTCAAGGAAAAAA
ATGTTCATATGCAAGAAAAAATGTTATCATTACCAGATGATCCAGCAATCTAGCAATATATAT
ATTGTTTATTCACAAAACATGAATGAACCTTTTAAGAAGCTGTTACAGTGTAAAAATTAAGTT
AAATCACTGAAGAACATATACTGTGTGATTTCATTCAAATGAAATTTGAGAAGTAAATATATA
TGTATATATATATATGTAAAAAATATAAGTCTGAACTACAAAAATTCAATTTGTTTGATAT
GTAAGAATAAGAAAAATTGACCCCCAAAATTTGTTAATAATTAGGTATGTGTATTTTATGAA
TATATAAGTATAATAATGCTTATAGTATACACTATTCTGAATCACATTTATTCCCTAAGTGTGT
TCCCTTGATTATAATTAAAAGTATATTTTTAAATACAGAGTCAGAGTACAGTCAATAAGGCG
AAAATATAGTTGAATGATTTGCTTCAGCTTTTGTAATGTACTAGAGATTGTGAGTACAAAGTC
TCAGAGCTCATTTTATCCCTGACAATAACCAGCTCTGTGCTTCAAGTACATTTCCATCTTTCTC
TGAAATTTAGTCTTATATAGATAGACAAAATTTAAGTAAATTTCAAACTACACAGAACAACTA
AGTTGTTGTTTCATATTGATAATGGATTTGAACTGCATTAACAGACTTTAACATCCTGCTTAT
TCTCCCTTCAGCCATCATATTTTGCTTTATTATTTTCACTTTTTGAGTTATTTTTCACATTCAGA
AAGCTCACATAATTGTCACTTCTTTGTATACTGGTATACAGACCAGAACATTTGCATATTGTTC
CCTGGGGAGGTCTTTGCCCTGTTGGCCTGAGATAAAACCTCAAGTGTCCTCTTGCCTCCACTGA
TCACTCTCCTATGTTTATTTCCTCAAA Mouse Igkv 1-133 exon 1 (leader) (SEQ ID No. 9):
ATGATGAGTCCTGCCCAGTTCCTGTTTCTGTTAGTGCTCTGGATTCAGG Mouse Igkv 1-133 intron 1 (SEQ ID No. 10):
GTAAGGAGTTTTGGAATGTGAGGGATGAGAATGGGGATGGAGGGTGATCTCTGGATGCCTAT
GTGTGCTGTTTATTTGTGGTGGGGCAGGTCATATCTTCCAGAATGTGAGGTTTTGTTACATCCT
AATGAGATATTCCACATGGAACAGTATCTGTACTAAGATCAGTATTCTGACATAGATTGGATG
GAGTGGTATAGACTCCATCTATAATGGATGATGTTTAGAAACTTCAACACTTGTTTTATGACA
AAGCATTTGATATATAATATTTTTAAATCTGAAAAACTGCTAGGATCTTACTTGAAAGGAATA
GCATAAAAGATTTCACAAAGGTTGCTCAGGATCTTTGCACATGATTTTCCACTATTGTATTGTA
ATTTCAG Mouse Igkv 1-133 5' part of exon 2 (leader) (SEQ ID No. 11):
AAACCAACGGT Cow Vκ from LOC100294952 (SEQ ID No. 12):
Gatccagtggggatgttgtgctgacccagactccactctccctgtctatcatccctgga-
gagatggcctccatctcctgcaagtctagtcagagcc
tggtacacagtgatggaaaaacctatttgaattggattcaatataaaccaggccaatcac-
cacagggtctgatctatcaggtttccaaccgttact
ctggggtctcagacaggttcactggcagtgggtcagggacagatttcacacttacaatca-
gcagagtgcaggctgaggatgctggagtctattact
gttaccaaggtacagaagat Mouse RSS heptamer
CACAGTG Mouse sequence downstream of RSS heptamer (SEQ ID No. 13):
ATACAGACTCTATCAAAAACTTCCTTGCCTGGGGCAGCCCAGCTGACAATGTGCAATCTGAAG
AGGAGCAGAGAGCATCTTGTGTCTGTGTGAGAAGGAGGGGCTGGGATACATGAGTAATTCTT
TGCAGCTGTGAGCTCTG

---

I claim:

1. A transgenic mouse with a genome in which a mouse endogenous immunoglobulin variable gene locus has been deleted and replaced with an engineered partly bovine immunoglobulin locus comprising bovine immunoglobulin variable gene $V_H$, $D_H$ and $J_H$ and/or bovine $V_L$ and $J_L$ coding sequences and mouse immunoglobulin variable gene locus non-coding regulatory and/or scaffold sequences, wherein the engineered partly bovine immunoglobulin locus of the transgenic mouse is functional and expresses immunoglobulin chains comprised of bovine variable domains and mouse constant domains.

2. An isolated B lymphocyte from the transgenic mouse of claim 1.

3. The transgenic mouse of claim 1, wherein the non-coding regulatory sequences comprise a promoter, preceding individual V gene segments, splice sites, and recombination signal sequences for V(D)J recombination.

4. The transgenic mouse of claim 1, wherein the engineered partly bovine immunoglobulin locus further comprises scaffold sequences comprising an ADAM6 gene.

5. The transgenic mouse of claim 1, wherein the engineered partly bovine immunoglobulin locus further comprises scaffold sequences comprising Pax-5-Activated Intergenic Repeat (PAIR) elements.

6. The transgenic mouse of claim 1, wherein the engineered partly bovine immunoglobulin locus further comprises scaffold sequences comprising CTCF binding sites from a heavy chain intergenic control region 1.

7. A method for generating the transgenic mouse of claim 1, said method comprising:
   a) integrating in a mouse's cell genome at least one target site for a site-specific recombinase in a mouse cell's genome upstream of an endogenous immunoglobulin variable gene locus and at least one target site for a site-specific recombinase downstream of the endogenous immunoglobulin variable gene locus, wherein the endogenous immunoglobulin variable locus comprises $V_H$, $D_H$ and $J_H$ gene segments, or Vκ and Jκ gene segments, or Vλ and Jλ gene segments, or Vλ, Jλ and Cλ gene segments;
   b) providing a vector comprising an engineered partly bovine immunoglobulin locus, said engineered partly bovine immunoglobulin locus comprising partly bovine immunoglobulin variable region segments, wherein each of the partly bovine immunoglobulin variable region gene segments comprises bovine immunoglobulin variable region gene $V_H$, $D_H$, and $J_H$ and/or bovine $V_L$ and $J_L$ coding sequences and mouse non-coding regulatory and/or scaffold sequences, with the partly bovine immunoglobulin variable region gene locus being flanked by target sites for a site-specific recombinase, wherein the target sites are capable of recombining with the target sites introduced into the mouse cell in step a);
   c) introducing into the cell the vector of step b) and a site-specific recombinase capable of recognizing the target sites;
   d) allowing a recombination event to occur between the genome of the cell and the engineered partly bovine immunoglobulin locus, resulting in a replacement of the endogenous immunoglobulin variable gene locus with the engineered partly bovine immunoglobulin locus;
   e) selecting a cell that comprises the engineered partly bovine immunoglobulin variable locus generated in step d); and
   utilizing the cell to create a transgenic mouse comprising the engineered partly bovine immunoglobulin variable locus.

8. The method of claim 7, wherein the cell is a mouse embryonic stem (ES) cell.

9. The method of claim 7, further comprising after the introducing step and before the providing step a step of deleting the endogenous immunoglobulin variable gene locus by introduction of a recombinase that recognizes a first set of target sites, wherein the deleting step leaves in place at least two target sites in the mouse cell's genome, where the second set of target sites are not capable of recombining with one another.

10. The method of claim 7, wherein the vector further comprises V gene promoters, splice sites, and recombination signal sequences to permit V(D)J recombination.

11. The method of claim 7, wherein the vector further comprises scaffold sequences comprising an ADAM6 gene.

12. The method of claim 7, wherein the vector further comprises scaffold sequences comprising Pax-5-Activated Intergenic Repeat elements.

13. The method of claim 7, wherein the vector further comprises scaffold sequences comprising CTCF binding sites from a heavy chain intergenic control region 1.

* * * * *

UNITED STATES PATENT AND TRADEMARK OFFICE
CERTIFICATE OF CORRECTION

PATENT NO. : 10,793,829 B2
APPLICATION NO. : 15/603347
DATED : October 6, 2020
INVENTOR(S) : Matthias Wabl It is certified that error appears in the above-identified patent and that said Letters Patent is hereby corrected as shown below:

In the Claims

Column 58, Line 32 (Claim 7): "utilizing the cell to create a transgenic mouse comprising the engineered partly bovine immunoglobulin variable locus." should be replaced with -- f) utilizing the cell to create a transgenic mouse comprising the engineered partly bovine immunoglobulin variable locus. --

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*